(12) United States Patent
Vikbjerg et al.

(10) Patent No.: US 11,173,178 B2
(45) Date of Patent: Nov. 16, 2021

(54) LIPOSOMES FOR DRUG DELIVERY AND METHODS FOR PREPARATION THEREOF

(71) Applicant: LiPlasome Pharma ApS, Vejle (DK)

(72) Inventors: Anders Falk Vikbjerg, Greve (DK); Sune Allan Petersen, Greve (DK); Fredrik Melander, Malmö (SE); Jonas Rosager Henriksen, Allerød (DK); Kent Jørgensen, Bagsværd (DK)

(73) Assignee: LiPlasome Pharma ApS, Vejle (DK)

( * ) Notice: Subject to any disclaimer, the term of this patent is extended or adjusted under 35 U.S.C. 154(b) by 0 days.

(21) Appl. No.: 16/786,194

(22) Filed: Feb. 10, 2020

(65) Prior Publication Data

US 2020/0171080 A1     Jun. 4, 2020

Related U.S. Application Data

(63) Continuation of application No. 12/994,031, filed as application No. PCT/EP2009/056297 on May 25, 2009, now abandoned.

(30) Foreign Application Priority Data

May 23, 2008   (DK) .......................... PA 2008 00717
Aug. 20, 2008  (EP) .................................... 08014793

(51) Int. Cl.
    *A61K 9/127*      (2006.01)
    *A61K 33/243*     (2019.01)
    (Continued)

(52) U.S. Cl.
    CPC .......... *A61K 33/243* (2019.01); *A61K 9/1271* (2013.01); *A61K 31/19* (2013.01);
    (Continued)

(58) Field of Classification Search
    CPC ...... A61K 33/24; A61K 31/519; A61K 38/14; A61K 31/203; A61K 31/19; A61K 31/704;
    (Continued)

(56) References Cited

U.S. PATENT DOCUMENTS

| | | |
|---|---|---|
| 4,880,635 A | 11/1989 | Janoff et al. |
| 4,963,362 A | 10/1990 | Rahman et al. |

(Continued)

FOREIGN PATENT DOCUMENTS

| | | |
|---|---|---|
| CA | 2428112 A1 | 11/2003 |
| EP | 2123258 A1 | 11/2009 |

(Continued)

OTHER PUBLICATIONS

Murakami, M., et al in BBA, 1488, pp. 159-166, 2000.*

(Continued)

*Primary Examiner* — Gollamudi S Kishore
(74) *Attorney, Agent, or Firm* — Clark & Elbing LLP

(57) ABSTRACT

The present invention provides liposomes that are useful for delivery of bioactive agents such as therapeutics. Among others, the liposomes of the invention are capable of delivering their payload at sites of increased secretory phospholipase A2 (sPLA2) activity, because phospholipase A2 (PLA2) will hydrolyse lipids of the liposome. Thus, the liposomes of the invention may e.g. be used in relation to cancer therapy. Another aspect of the invention is a liposomal formulation comprising the liposome of the invention. Still another aspect is a method of producing a liposomal formulation of the invention.

13 Claims, 27 Drawing Sheets

(51) Int. Cl.

| | |
|---|---|
| *A61K 31/555* | (2006.01) |
| *A61K 31/192* | (2006.01) |
| *A61K 31/203* | (2006.01) |
| *A61K 31/337* | (2006.01) |
| *A61K 31/19* | (2006.01) |
| *A61K 38/14* | (2006.01) |
| *A61K 31/475* | (2006.01) |
| *A61K 31/704* | (2006.01) |
| *A61K 31/519* | (2006.01) |
| *A61K 31/513* | (2006.01) |

(52) U.S. Cl.
CPC .......... *A61K 31/192* (2013.01); *A61K 31/203* (2013.01); *A61K 31/337* (2013.01); *A61K 31/475* (2013.01); *A61K 31/513* (2013.01); *A61K 31/519* (2013.01); *A61K 31/555* (2013.01); *A61K 31/704* (2013.01); *A61K 38/14* (2013.01)

(58) Field of Classification Search
CPC .. A61K 31/475; A61K 31/337; A61K 31/555; A61K 9/1271; A61K 31/513; A61K 31/192; A61K 33/243; A61P 35/00; A61P 31/10; A61P 31/04; A61P 31/00; A61P 29/00
See application file for complete search history.

(56) References Cited

U.S. PATENT DOCUMENTS

| | | | |
|---|---|---|---|
| 5,858,397 A | 1/1999 | Lim et al. | |
| 6,027,726 A | 2/2000 | Ansell | |
| 6,911,306 B1 | 6/2005 | Vertino | |
| 7,273,620 B1 | 9/2007 | Zhigaltsev et al. | |
| 9,820,941 B2 | 11/2017 | Madsen et al. | |
| 2003/0026831 A1* | 2/2003 | Lakkaraju | A61K 9/127 424/450 |
| 2003/0147945 A1 | 8/2003 | Tardi et al. | |
| 2004/0022842 A1* | 2/2004 | Eriguchi | A61K 31/555 424/450 |
| 2005/0118250 A1 | 6/2005 | Tardi et al. | |
| 2005/0222396 A1 | 10/2005 | Bao et al. | |
| 2006/0105360 A1 | 5/2006 | Croce et al. | |
| 2007/0148196 A1 | 6/2007 | Haas et al. | |
| 2007/0286898 A1 | 12/2007 | Takagi et al. | |
| 2008/0085295 A1* | 4/2008 | Melvik | A61K 9/0024 424/423 |
| 2008/0306006 A1 | 12/2008 | Croce et al. | |
| 2009/0162425 A1 | 6/2009 | Divi et al. | |
| 2010/0189771 A1 | 7/2010 | Mayer et al. | |
| 2012/0009243 A1 | 1/2012 | Vikbjerg et al. | |
| 2012/0177726 A1 | 7/2012 | Petersen et al. | |
| 2012/0214703 A1 | 8/2012 | Croce et al. | |
| 2018/0202004 A1 | 7/2018 | Knudsen | |

FOREIGN PATENT DOCUMENTS

| | | |
|---|---|---|
| KR | 10-2007-0036055 A | 4/2007 |
| WO | WO-99/30686 A1 | 6/1999 |
| WO | 2005/000266 * | 1/2005 |
| WO | WO-2005/000266 A2 | 1/2005 |
| WO | WO-2005/005601 A2 | 1/2005 |
| WO | WO-2009/141450 A2 | 11/2009 |
| WO | WO-2011/032563 A1 | 3/2011 |
| WO | WO-2011/047689 A2 | 4/2011 |
| WO | WO-2011/098578 A2 | 8/2011 |

OTHER PUBLICATIONS

Andresen, T. L., et al in Progress in Lipid Research, 44, pp. 68-97, 2005.*

Arienti et al., "Activity of lipoplatin in tumor and in normal cells in vitro," Anti-Cancer Drugs. 19(10):983-990 (2008) (8 pages).

Andresen et al., "Advanced strategies in liposomal cancer therapy: problems and prospects of active and tumor specific drug release," Prog Lipid Res. 44(1):68-97 (2005).

Boulikas, "Clinical overview on Lipoplatin™: a successful liposomal formulation of cisplatin," Expert Opin Investig Drugs. 18(8):1197-218 (2009) (23 pages).

Buhl et al., "Molecular prediction of adjuvant cisplatin efficacy in Non-Small Cell Lung Cancer (NSCLC)—validation in two independent cohorts," PLoS One.13(3): e0194609 (2018) (12 pages).

Casagrande et al., "Preclinical Activity of the Liposomal Cisplatin Lipoplatin in Ovarian Cancer," Clin Cancer Res. 20(21):5496-5506 (12 pages).

de Jonge et al., "Early cessation of the clinical development of LiPlaCis, a liposomal cisplatin formulation," Eur J Cancer. 46(16):3016-3021 (2010) (6 pages).

Extended European Search Report for European Application No. 18172585.4, dated Oct. 9, 2018 (7 pages).

Extended European Search Report for European Patent Application No. 19154186.1, dated Jun. 7, 2019 (9 pages).

English Translation of Decision / Order of Hearing of the Patent Application for Indian Patent Application No. 4565/KOLNP/2010, dated Sep. 8, 2017 (1 page).

Extended European Search Report for European Patent Application No. 17211034.8, dated May 22, 2018 (13 pages).

Liang et al., "Characterization of microRNA expression profiles in normal human tissues," BMC Genomics. 8(166):1-20 (2007).

Meerum Terwogt et al., "Phase I and pharmacokinetic study of SPI-77, a liposomal encapsulated dosage form of cisplatin," Cancer Chemother Pharmacol. 49(3):201-10 (2002).

Murakami et al., "Cellular components that functionally interact with signaling phospholipase A(2)s," Biochim Biophys Acta. 1488(1-2):159-66 (2000).

"Oncology Venture presents LiPlaCis on AACR in New Orleans," Press release issued by Oncology Venture Sweden AB, Hoersholm, Denmark, Mar. 4, 2016 (2 pages).

Østrem et al., "Secretory phospholipase A2 responsive liposomes exhibit a potent anti-neoplastic effect in vitro, but induce unforeseen severe toxicity in vivo," J Control Release. 262: 212-221 (2017).

Pourhassan et al., "Revisiting the use of sPLA2-sensitive liposomes in cancer therapy," J Control Release. 261:163-173 (2017).

Veal et al., "A phase I study in paediatric patients to evaluate the safety and pharmacokinetics of SPI-77, a liposome encapsulated formulation of cisplatin," Br J Cancer. 84(8):1029-35 (2001).

Bentz et al., "Temperature dependence of divalent cation induced fusion of phosphatidylserine liposomes: evaluation of the kinetic rate constants," Biochemistry 24(4):1064-72 (1985).

Buckland et al., "Anionic phospholipids, interfacial binding and the regulation of cell functions," Biochim. Biophys. Acta 1483(2):199-216 (2000).

Buckland et al., "Bacterial cell membrane hydrolysis by secreted phospholipases A(2): a major physiological role of human group IIa sPLA(2) involving both bacterial cell wall penetration and interfacial catalysis," Biochim. Biophys. Acta 1484(2-3):195-206 (2000).

Chonn et al., "The role of surface charge in the activation of the classical and alternative pathways of complement by liposomes," J. Immunol. 146(12):4234-41 (1991).

Düzgünes et al., "Calcium- and magnesium-induced fusion of mixed phosphatidylserine/phosphatidylcholine vesicles: effect of ion binding," J. Membr. Biol. 59(2):115-25 (1981).

Epand et al., "Effect of electrostatic repulsion on the morphology and thermotropic transitions of anionic phospholipids," FEBS Lett. 209(2):257-60 (1986).

Jerremalm et al., "Alkaline hydrolysis of oxaliplatin—isolation and identification of the oxalato monodentate intermediate," J. Pharm. Sci. 91(10):2116-21 (2002).

Jerremalm et al., "Hydrolysis of oxaliplatin-evaluation of the acid dissociation constant for the oxalato monodentate complex," J. Pharm. Sci. 92(2):436-8 (2003).

Jerremalm et al., "Oxaliplatin degradation in the presence of chloride: identification and cytotoxicity of the monochloro monooxalato complex," Pharm. Res. 21(5):891-4 (2004).

(56) References Cited

OTHER PUBLICATIONS

Jerremalm et al., "Oxaliplatin degradation in the presence of important biological sulphur-containing compounds and plasma ultrafiltrate," Eur. J. Pharm. Sci. 28(4):278-83 (2006).
Jorgensen et al., "Biophysical mechanisms of phospholipase A2 activation and their use in liposome-based drug delivery," FEBS Lett. 531(1): 23-7 (2002).
Kenworthy et al., "Range and magnitude of the steric pressure between bilayers containing phospholipids with covalently attached poly(ethylene glycol)," Biophys. J. 68(5):1921-36 (1995).
Kenworthy et al., "Structure and phase behavior of lipid suspensions containing phospholipids with covalently attached poly(ethylene glycol)," Biophys. J. 68(5):1903-20 (1995).
Leung et al., "Phospholipase A2 group IIA expression in gastric adenocarcinoma is associated with prolonged survival and less frequent metastasis," Proc. Natl. Acad. Sci. USA. 99(25):16203-8 (2002).
Logisz et al., "Effect of salt concentration on membrane lysis pressure," Biochim. Biophys. Acta. 1717(2):104-8 (2005).
Narenji et al., "Effect of Charge on Separation of Liposomes upon Stagnation," Iran J. Pharm. Res. 16(2):423-431 (2017).
Needham et al., "Exchange of monooleoylphosphatidylcholine as monomer and micelle with membranes containing poly(ethylene glycol)-lipid," Biophys. J. 73(5):2615-29 (1997).
Praml et al., "Secretory type II phospholipase A2 (PLA2G2A) expression status in colorectal carcinoma derived cell lines and in normal colonic mucosa," Oncogene 17(15):2009-12 (1998).
Shoemaker et al., "Calcium modulates the mechanical properties of anionic phospholipid membranes," J. Colloid. Interface Sci. 266(2):314-21 (2003).
Szebeni et al., "Liposome-induced complement activation and related cardiopulmonary distress in pigs: factors promoting reactogenicity of Doxil and AmBisome," Nanomedicine 8(2):176-84 (2012).
Xu et al., "The effect of cholesterol domains on PEGylated liposomal gene delivery in vitro," Ther. Deilv. 2(4):451-60 (2011) (18 pages).
Zhu et al., "Secretory phospholipase A2 responsive liposomes," J. Pharm. Sci. 100(8):3146-3159 (2011).

\* cited by examiner

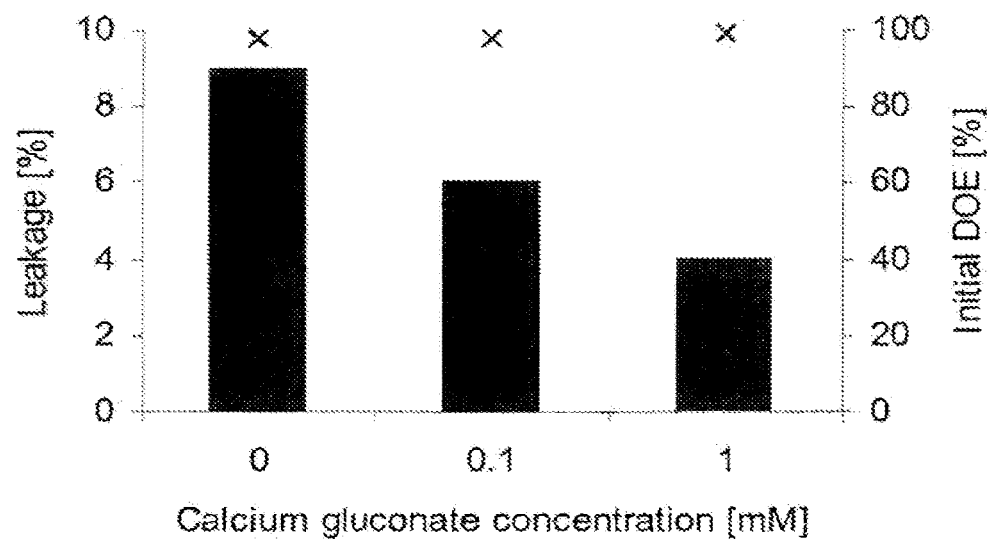
Figure 3A
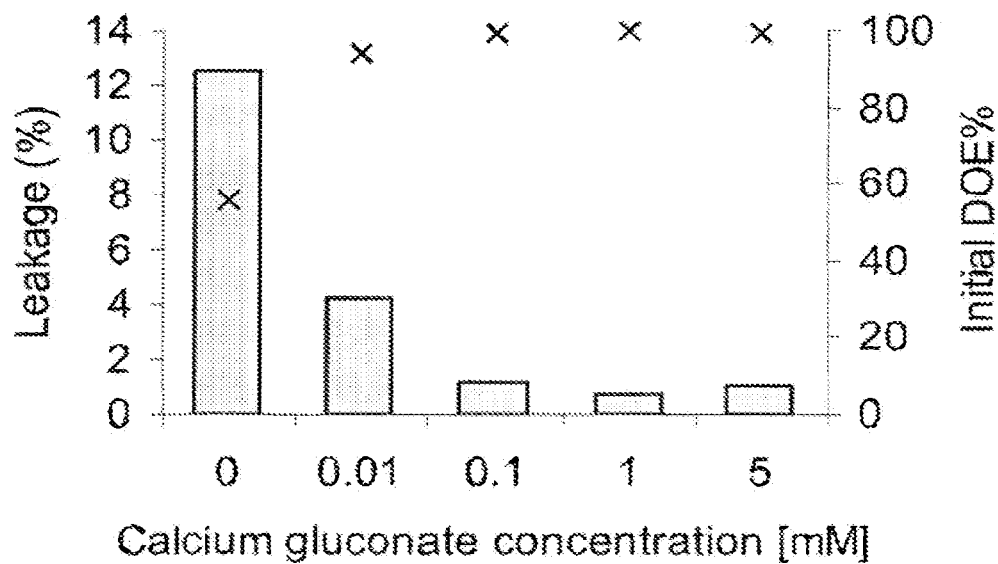
Figure 3B
Fig. 3

LIPOSOMES FOR DRUG DELIVERY AND METHODS FOR PREPARATION THEREOF

BACKGROUND OF THE INVENTION

Liposomes are microscopic spheres which were developed as drug delivery vehi-cles/systems in the 1980s. The first liposome-based pharmaceuticals were approved for commercial use in the 1990s.

Liposomes have three distinct compartments that can be used to carry various compounds such as, e.g. drugs: The interior aqueous compartment; the hydrophobic bilayer; and the polar inter-phase of the inner and outer leaflet. Depending on the chemical nature of the compound to be encapsulated it will be localised to either of the compartments. Currently, there are several parenteral liposome-drug formulations available on the market. Water soluble drugs tend to be localised in the aqueous compartment of liposomes, and examples of drugs encapsulated in liposome's are, e.g. doxorubicin (Doxil), doxorubicin (Myocet) and daunorubicin (DaunoXone). Examples of drugs intercalated in the liposome membrane are, e.g. amphotericin B (AmBisome), amphotericin (Albelcet B), benzoporphyrin (Visudyne) and muramyltripeptide-phosphatidylethanolamine (Junovan).

The liposome technology has thus provided intelligent solutions to solve challenges in pharmacology such as e.g. increase drug solubility, reduce drug toxicity, improve targeted drug release, etc.

The property of liposomes as drug delivery vehicles is crucially dependent on their surface charge, permeability, solubility, stability etc. which is significantly influenced by the lipids comprised in the liposome composition. In addition, the drug to be encapsulated in the liposome may need further requirements to be considered in preparing a stable liposome formulation.

Considerations regarding safety and drug efficacy require that liposome formulations maintain their properties, i.e. remain stable, from the time of preparation until administration. Furthermore, it is desirable that such formulations are intact during the transport in the treated subject until they reach the target site where the drug is specifically released. Thus there is still a need for obtaining improved liposome formulations.

SUMMARY OF THE INVENTION

In a first aspect, the present invention provides liposomes that are useful for delivery of bioactive agents such as therapeutics. Among others, the liposomes of the invention are capable of delivering their payload at sites of increased secretory phospholipase $A_2$ (s$PLA_2$) activity, because phospholipase $A_2$ ($PLA_2$) will hydrolyse lipids of the liposome. Thus, the liposomes of the invention may e.g. be used in relation to cancer therapy. A second aspect of the invention is a liposomal formulation comprising the liposome of the invention. Still another aspect is a method of producing a liposomal formulation of the invention.

DISCLOSURE OF THE INVENTION

Brief Description of the Drawing(s)

The invention is explained in detail below with reference to the drawing(s), in which FIG. 1 illustrates the UV spectra of oxaliplatin stored in solution containing 10% sucrose and 1 mM calcium gluconate during storage at room temperature.

FIG. 2 illustrates the relative absorbance (day/day 0) at 254 nm for oxaliplatin stored in a solution containing 10% sucrose and 1 mM calcium gluconate during storage at room temperature (FIG. 1).

FIG. 3 illustrates the effect of varying calcium gluconate concentrations on leakage from liposomes (70/25/5 mol % DSPC/DSPG/DSPE-PEG2000) containing cisplatin (A) or oxaliplatin (B) after 24 hours storage in cell media (McCoy) at 37° C. (primary axis). The initial degree of encapsulation (DOE) is marked on the secondary axis.

Figure 5:
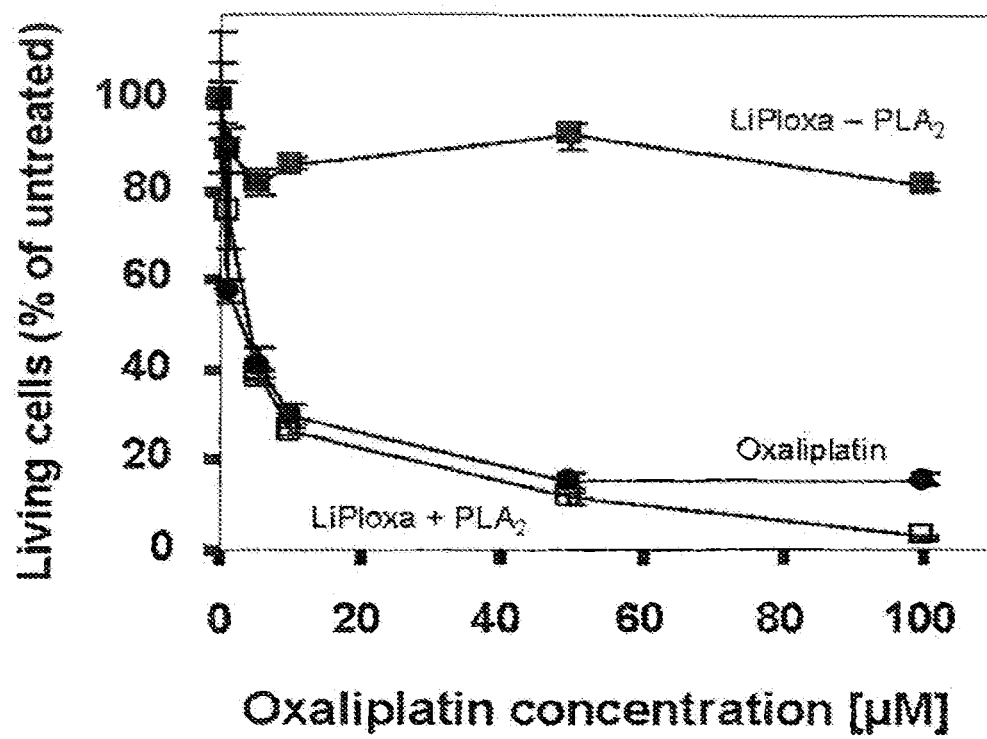
Figure 5:
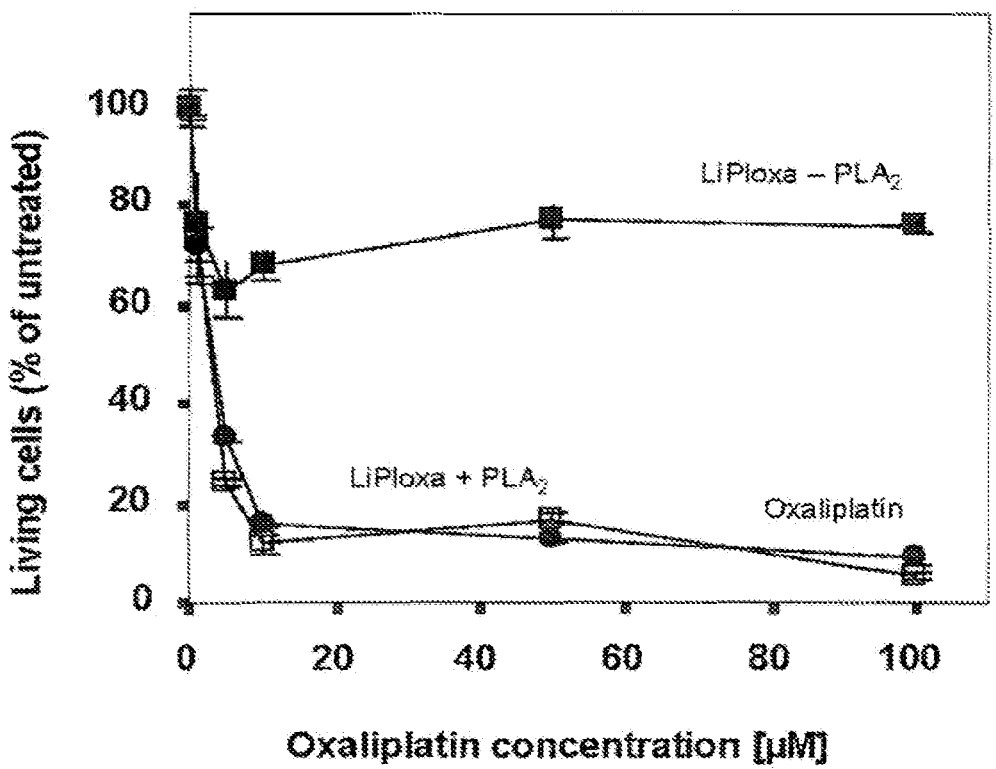
Figure 5:
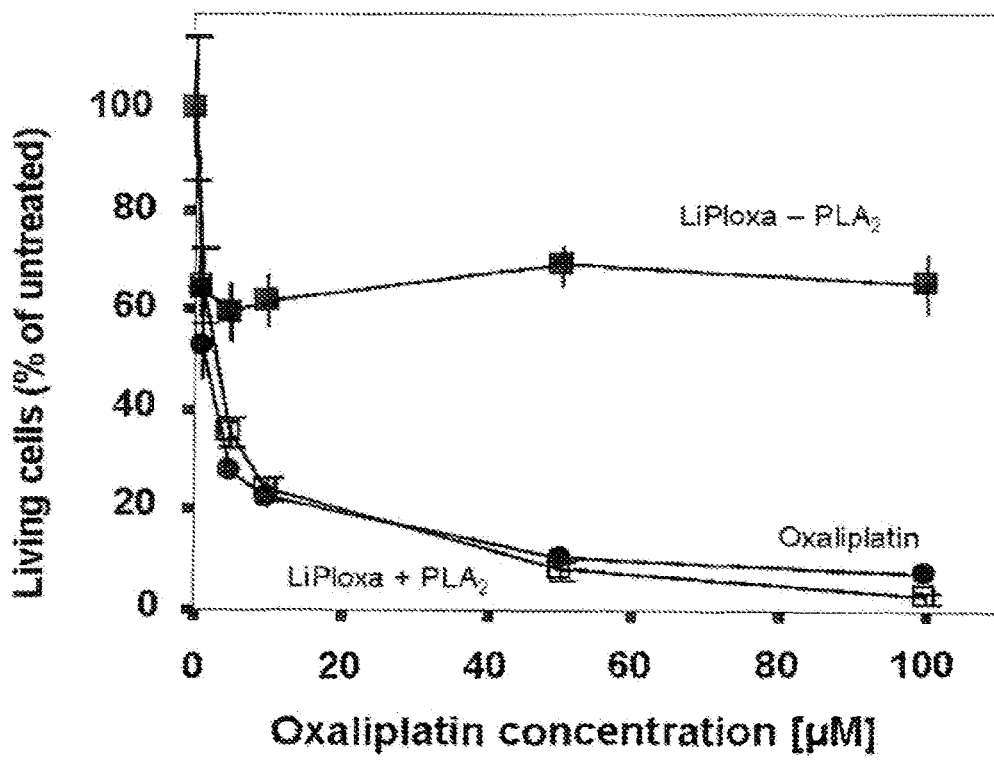
Figure 5:
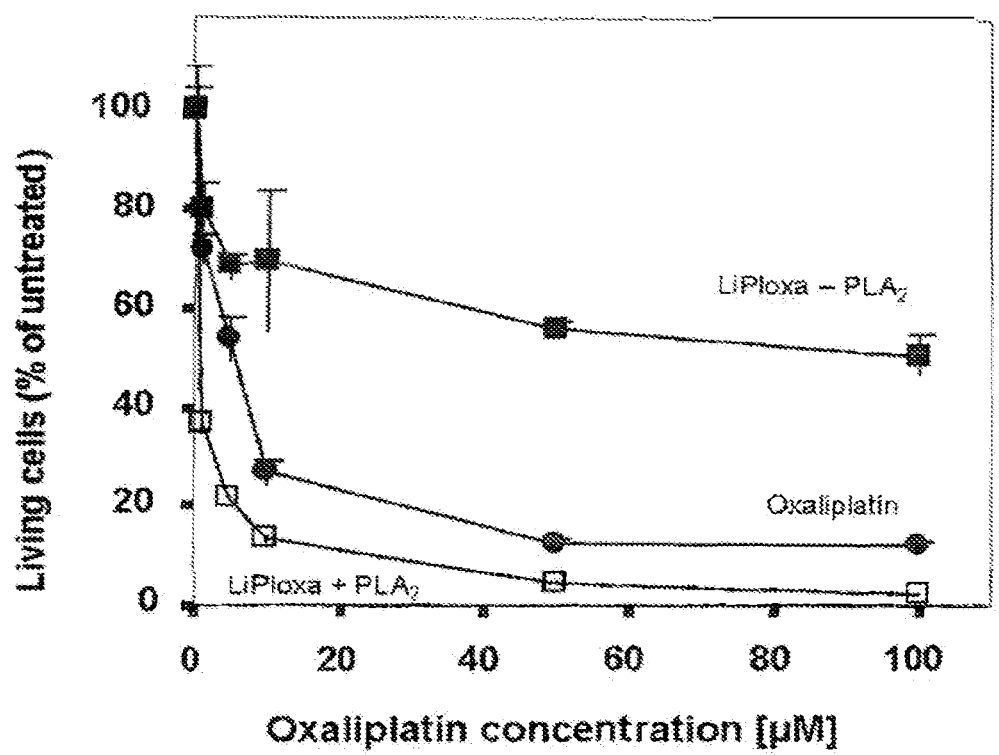
Figure 5:
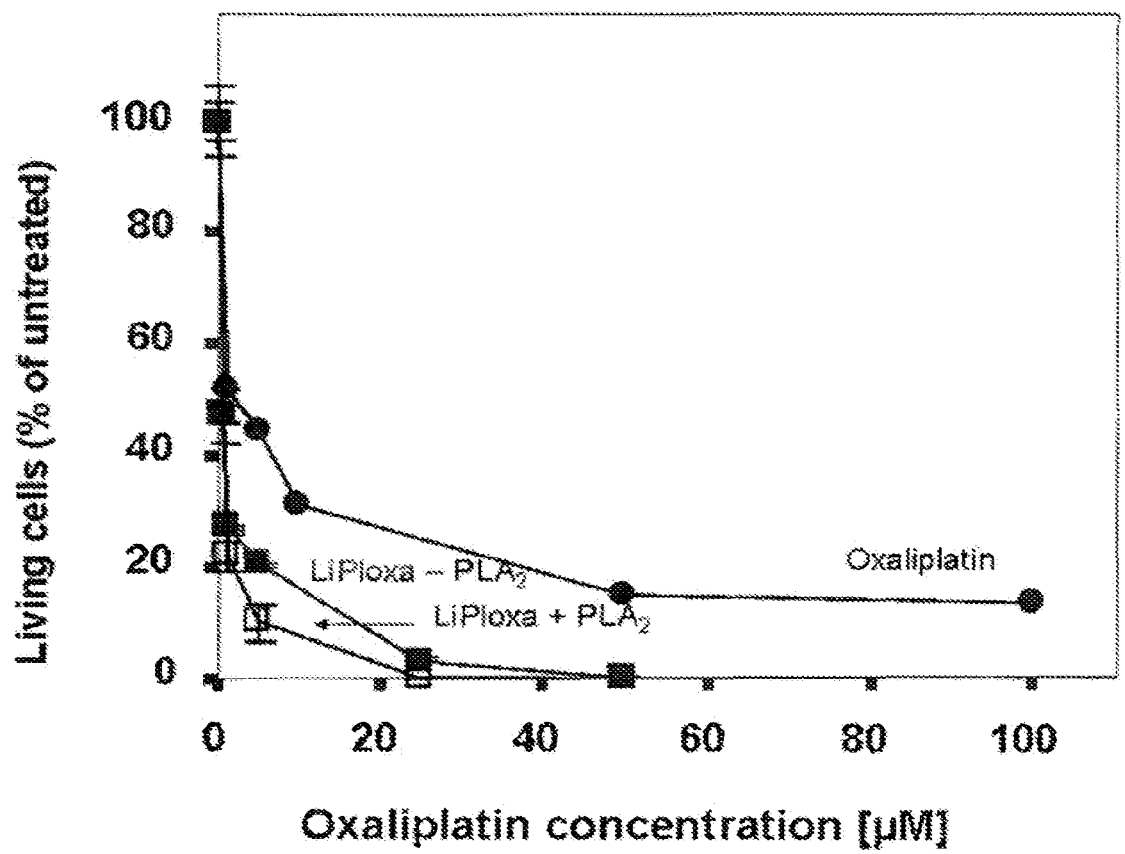

FIG. 5 illustrates the cytotoxicity of liposome (70/25/5 mol % DSPC/DSPG/DSPE-PEG2000) encapsulated oxaliplatin containing varying concentrations of calcium gluconate (A) 5 mM calcium gluconate, (B) 1 mM calcium gluconate, (C) 0.1 mM calcium gluconate, (D) 0.01 mM calcium gluconate, and (E) 0 mM calcium gluconate. HT-29 colon carcinoma cells were treated for 6 hours (37° C.) with oxaliplatin or Liposome encapsulated oxaliplatin in the presence or absence of s$PLA_2$.

Figure 6:
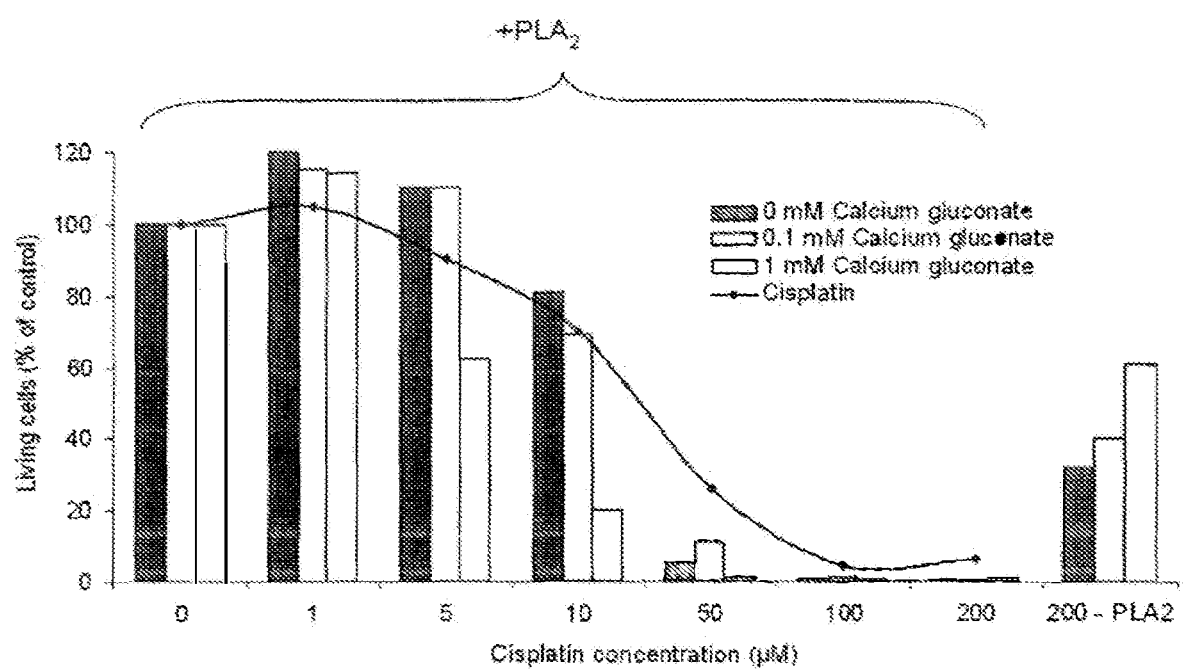

FIG. 6 illustrates the cytotoxicity of liposome (70/25/5 mol % DSPC/DSPG/DSPE-PEG2000) encapsulated cisplatin containing varying concentrations of calcium gluconate. HT-29 colon carcinoma cells were treated for 24 hours (37° C.) with cisplatin in the presence or absence of s$PLA_2$.

Figure 7:
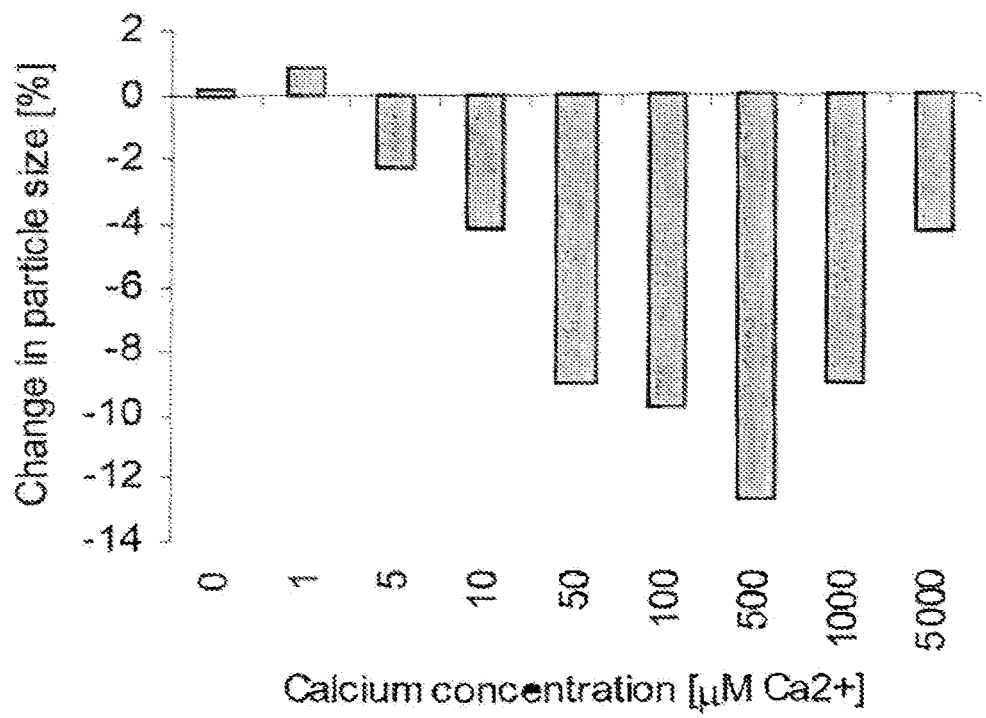

FIG. 7. Changes in particle size as function of calcium concentration for oxaliplatin encapsulated liposomes (70/25/5 mol % DSPC/DSPG/DSPE-PEG2000) containing no calcium after 24 h at room temperature. Lipid concentration maintained at 0.84 mM.

Figure 8:
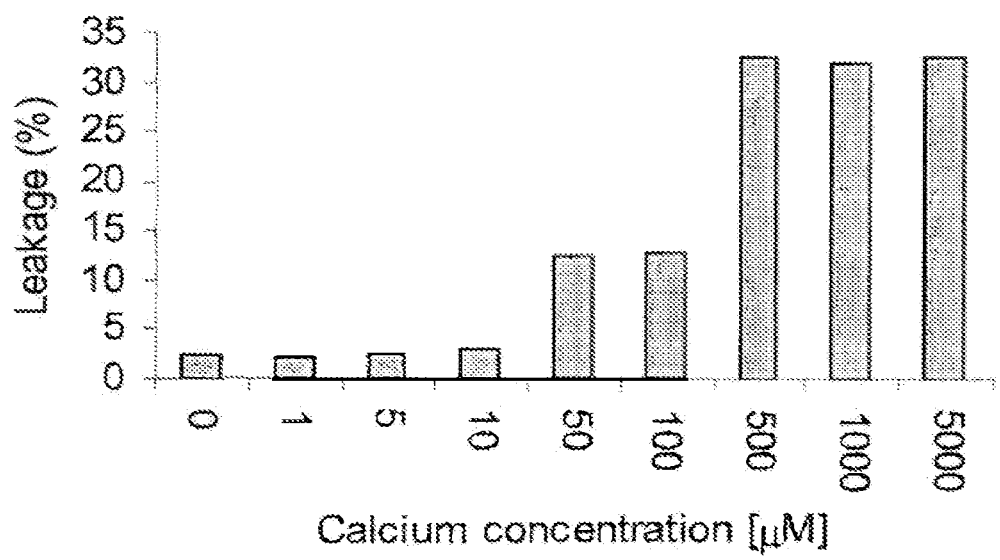

FIG. 8. Leakage from Liposome encapsulated oxaliplatin formulation (70/25/5 mol % DSPC/DSPG/DSPE-PEG2000) containing no calcium after 24 h at room temperature as a function of calcium concentration. Lipid concentration maintained at 0.84 mM.

Figure 9:
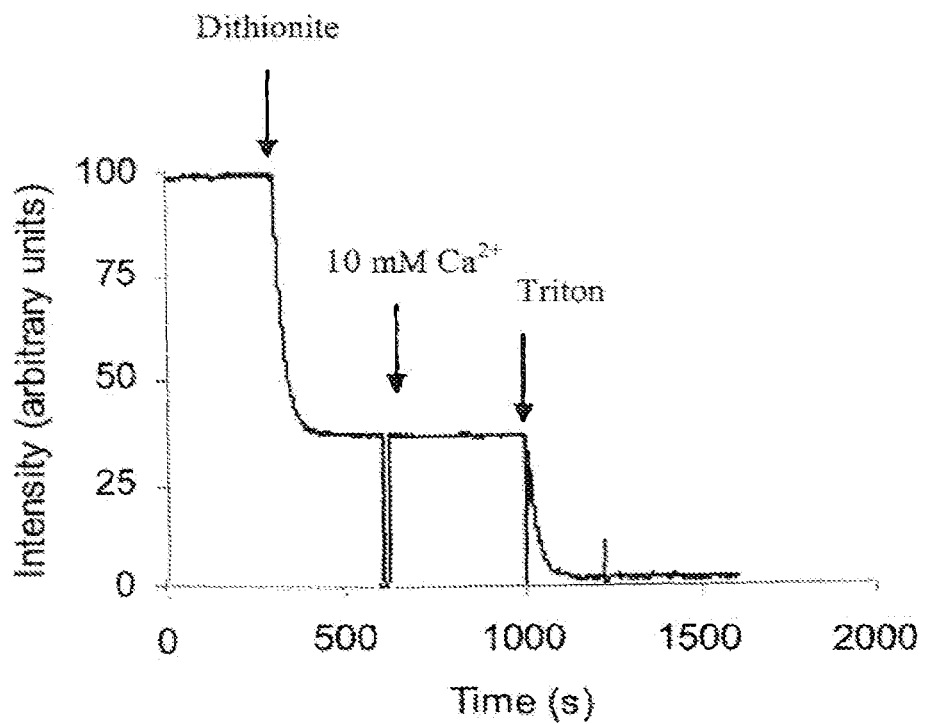

FIG. 9. The time-dependence of fluorescence intensity of DSPC/DSPG/DSPE-PEG LUV containing 0.5 mol % NBD-PE at 25° C. Arrow indicates the addition of dithionite, calcium and Triton-X100.

Figure 10:
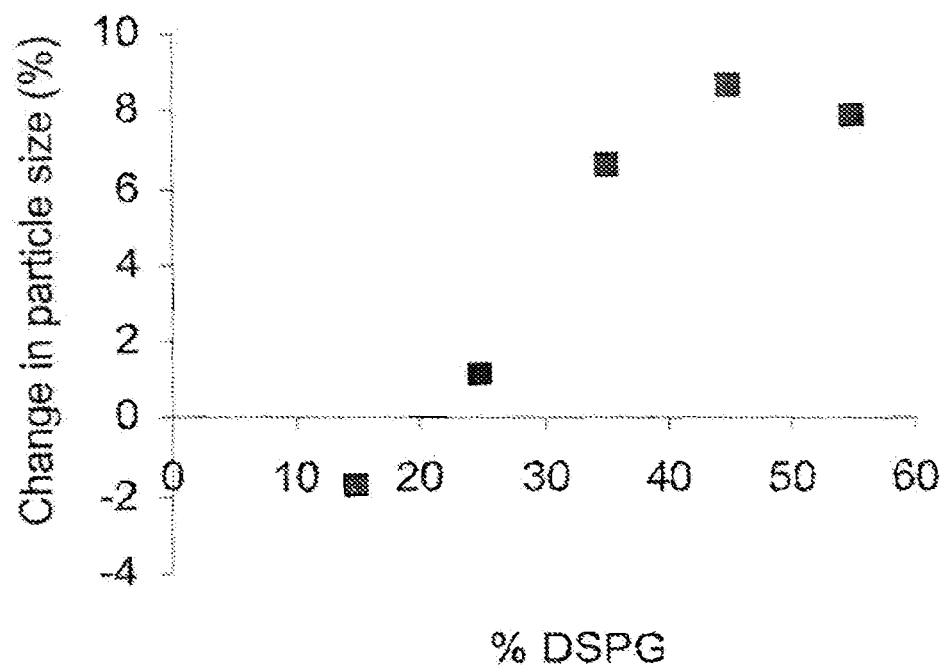

FIG. 10. Changes in particle size from sonication step to after 1st dialysis step (10% sucrose) as a function of DSPG in the liposomal oxaliplatin formulations containing 5 mol % DSPE-PEG2000 and DSPC.

Figure 11:
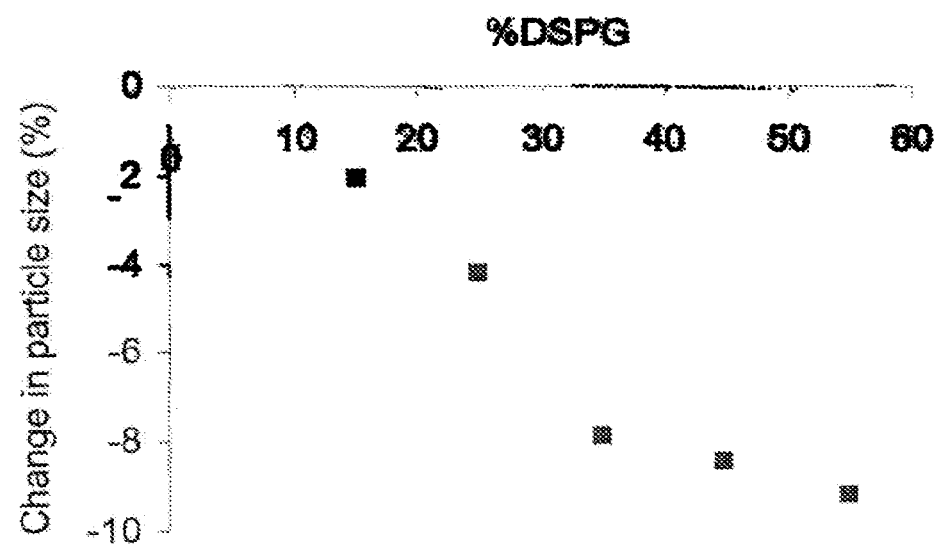

FIG. 11. Changes in particle size from 1st dialysis step (10% sucrose) to after 2nd dialysis step (10% sucrose+ calcium gluconate) as a function of DSPG in the liposomal oxaliplatin formulations containing 5 mol % DSPE-PEG2000 and DSPC.

Figure 12:
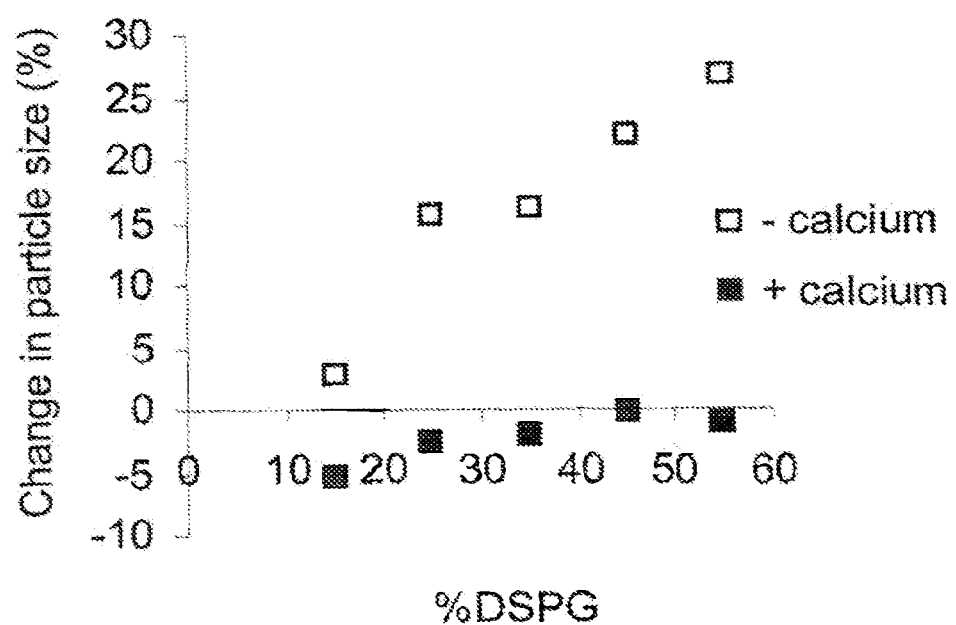

FIG. 12. Changes in particle size from sonication to after 2nd dialysis step (10% sucrose+/−calcium gluconate) as a function of DSPG in the liposomal oxaliplatin formulations containing DSPC and 5 mol % DSPE-PEG2000.

Figure 13:
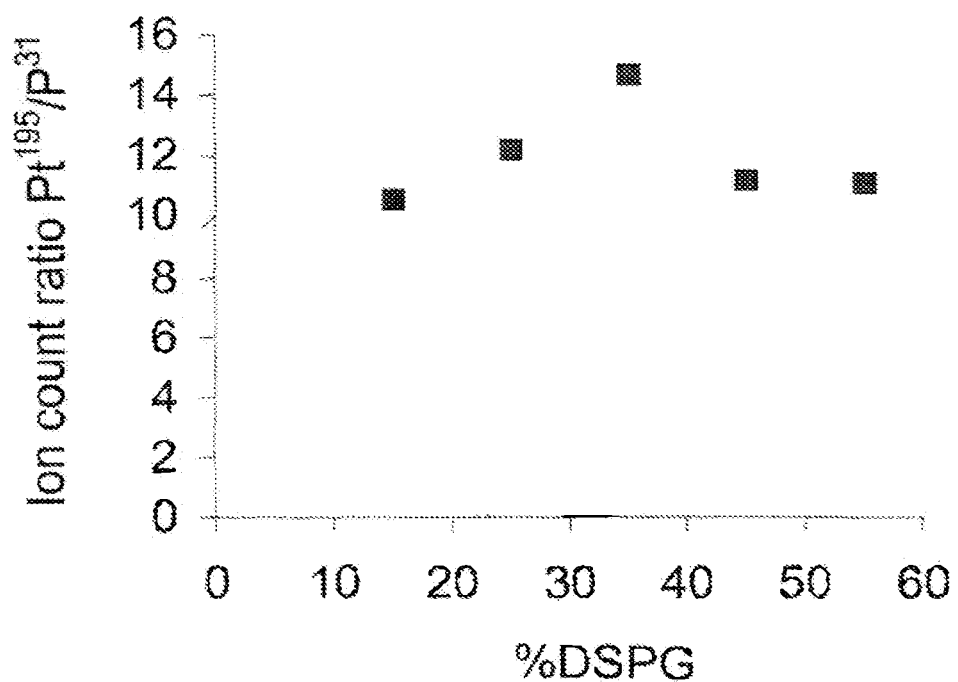

FIG. 13. Ion count ratio ($Pt^{195}/P^{31}$) for liposomal oxaliplatin formulations containing 5 mol % DSPE-PEG2000 and varying amounts of DSPC and DSPG after 1st dialysis step (10% sucrose solution).

Figure 14:
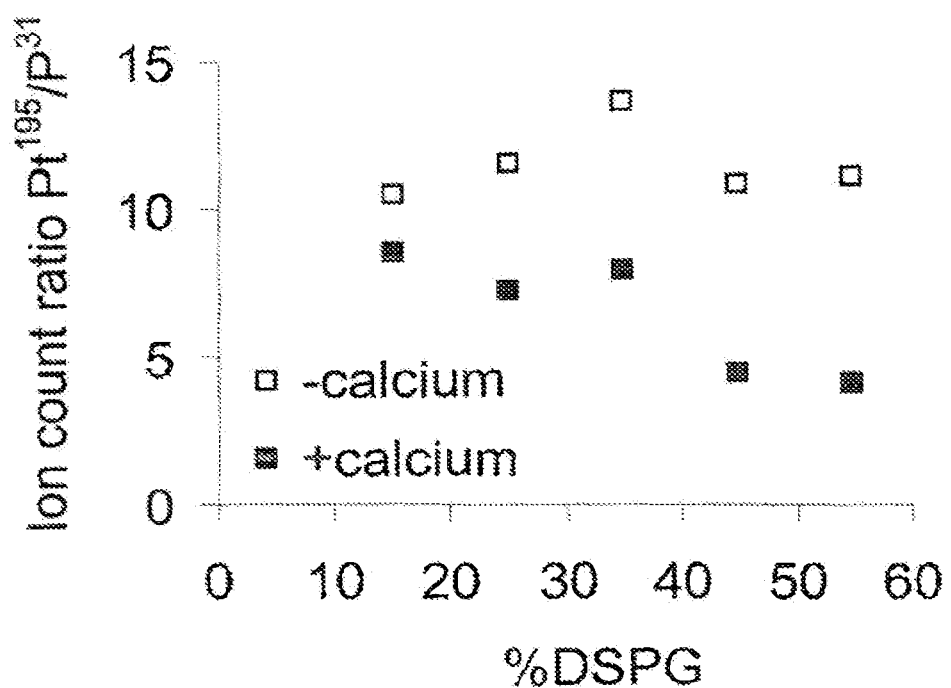

FIG. 14. Ion count ratio ($Pt^{195}/P^{31}$) for liposomal oxaliplatin formulations containing 5 mol % DSPE-PEG2000 and varying amounts of DSPC and DSPG after 2nd dialysis step (10% sucrose solution±1 mM calcium gluconate).

Figure 15:
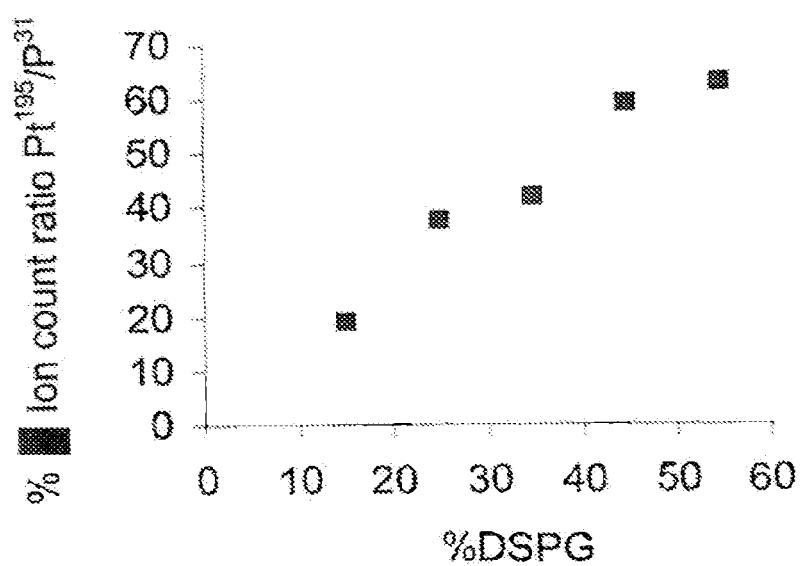

FIG. 15. %-difference in the ion count ratio ($Pt^{195}/P^{31}$) for formulations dialyzed in solution without calcium compared to formulations dialyzed with calcium (see FIG. 14).

Figure 16:
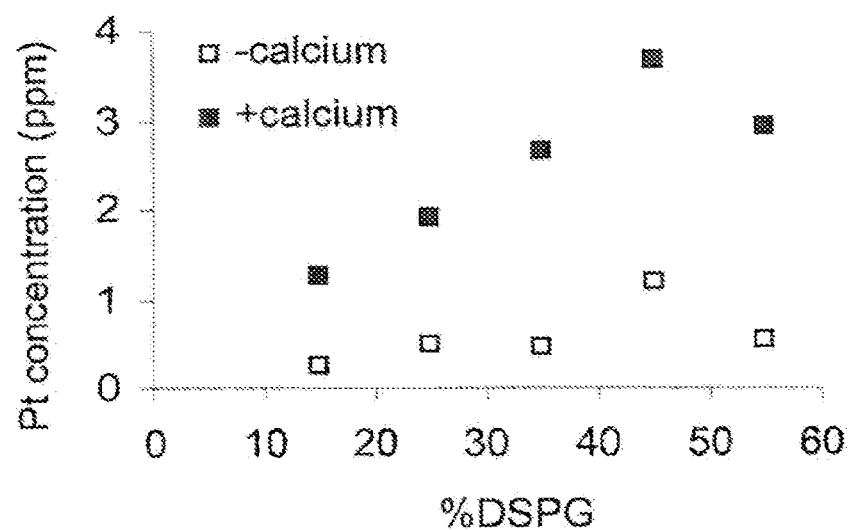

FIG. 16. Pt concentration in dialysate after 2nd dialysis (10% sucrose solution±1 mM calcium gluconate) of liposomal oxaliplatin formulations containing 5 mol % DSPE-PEG2000 and varying amounts of DSPC and DSPG.

Figure 17:
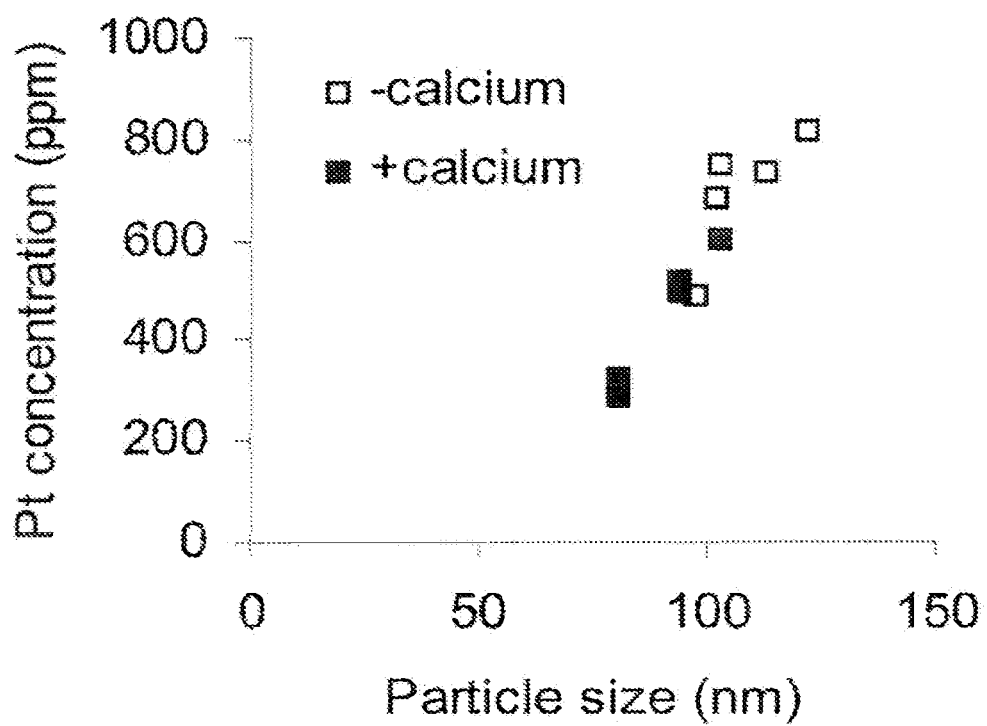

FIG. 17. Correlation between the final liposome size and concentration of oxaliplatin in formulations. Liposomal oxaliplatin formulations (5 mol % DSPE-PEG2000, and varying amounts of DSPC and DSPG) were prepared with or without 1 mM calcium gluconate during dialysis (see FIG. 14).

Figure 18:
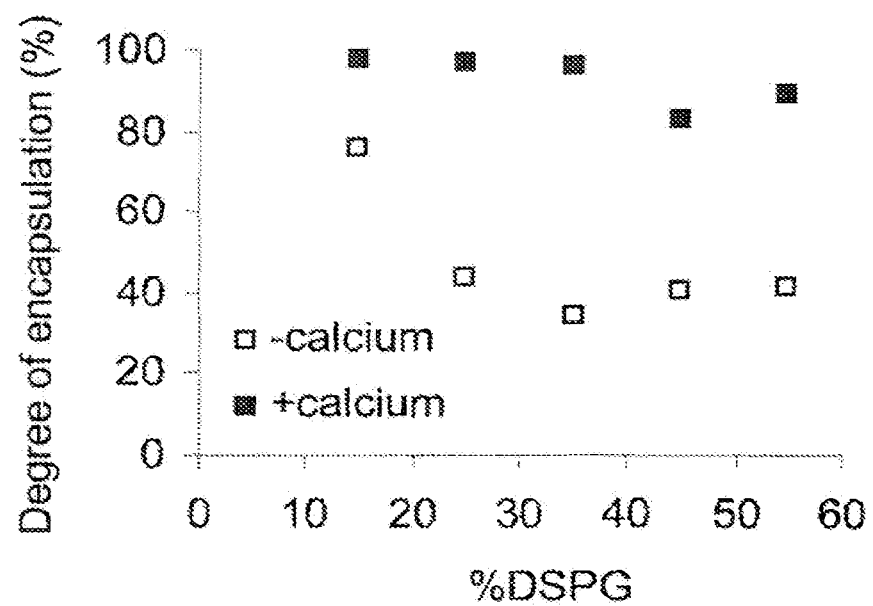

FIG. 18. Stability of liposomal oxaliplatin formulations (5 mol % DSPE-PEG2000, and varying concentrations of DSPC and DSPG) in McCoy cell media (24 h incubation at 37° C.).

Figure 19:
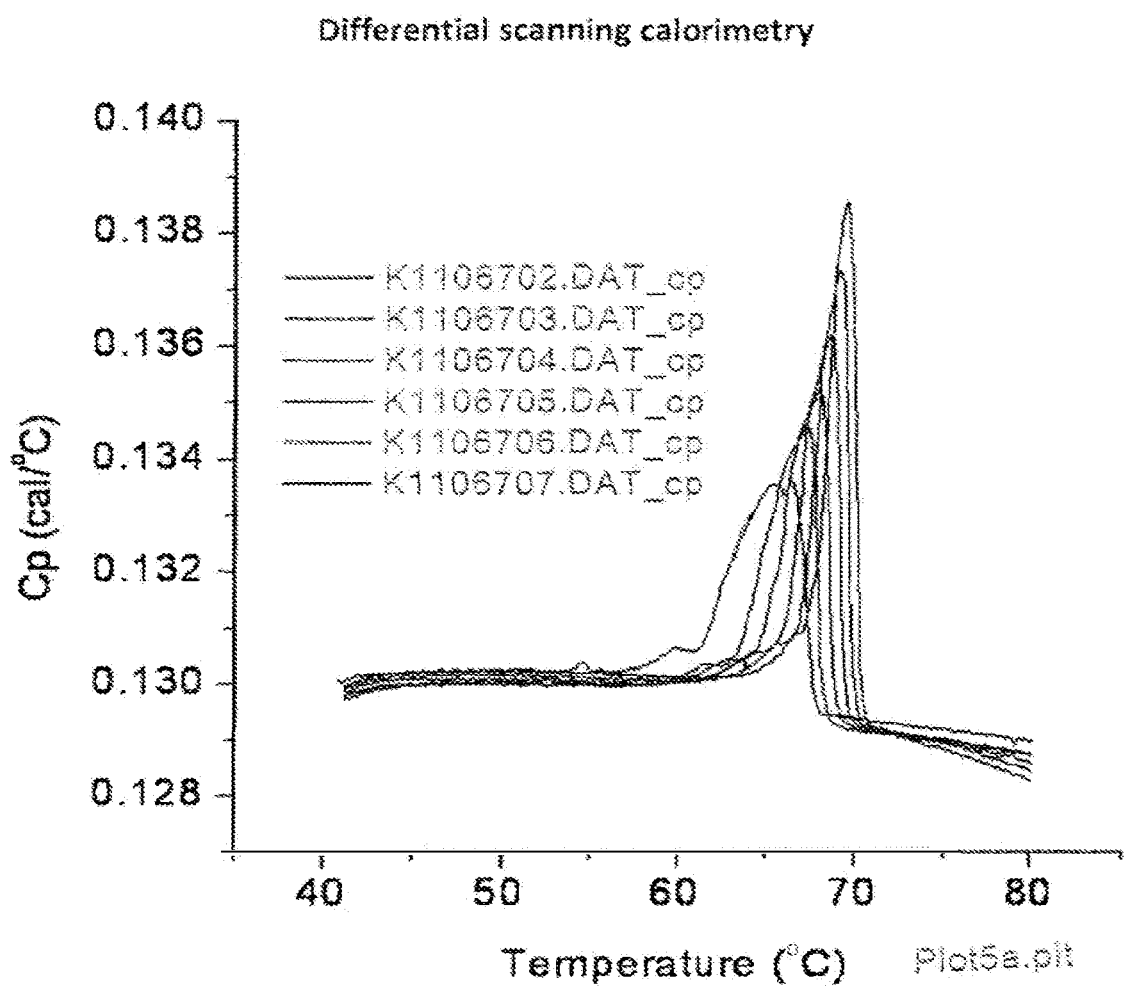

FIG. 19. 1.-6. DSC scans of Liposome encapsulated oxaliplatin (60/35/5 mol % DSPC/DSPG/DSPE-PEG2000) formulation without the presence calcium gluconate. Scan speed: 20° C./h.

Figure 20:
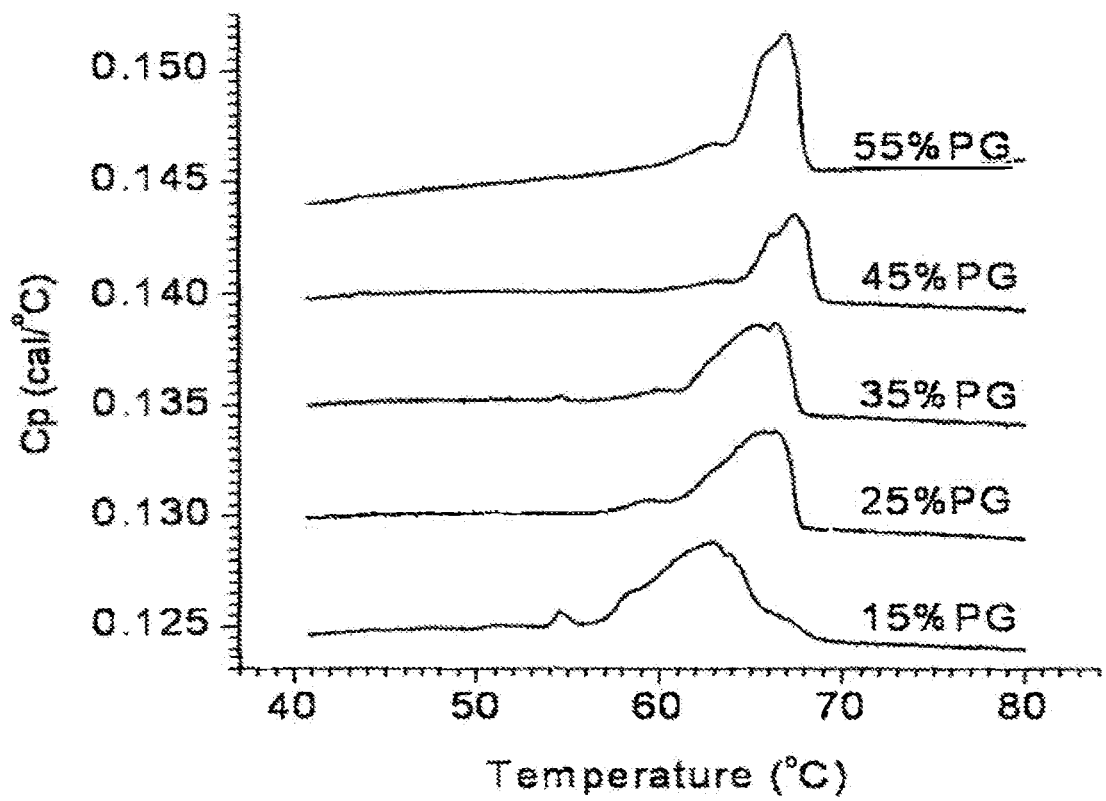

FIG. 20. DSC scan (1st scan) of Liposome encapsulated oxaliplatin formulations containing 5 mol % DSPE-PEG2000 and varying DSPC and DSPG concentrations and without the presence of calcium gluconate. Scan speed: 20° C./h.

Figure 21:
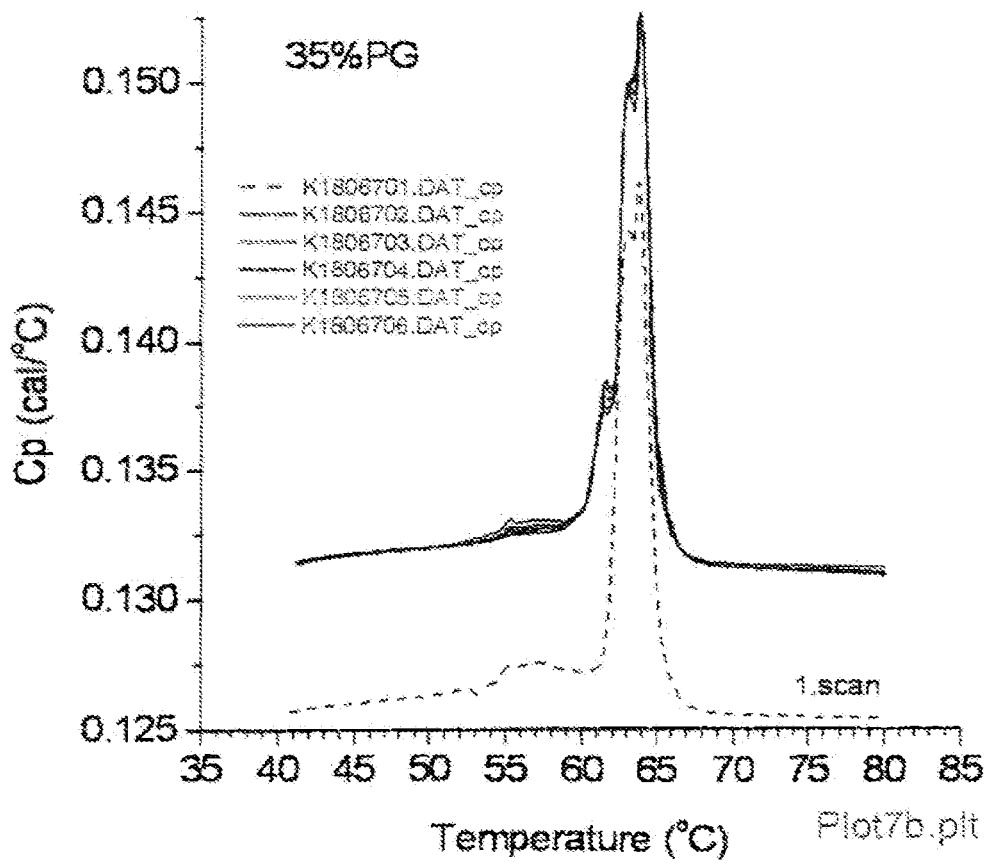

FIG. 21. 1.-6. DSC scans of Liposome encapsulated oxaliplatin (60/35/5 mol % DSPC/DSPG/DSPE-PEG2000) formulation with 1 mM calcium gluconate on the exterior. Scan speed: 20° C./h.

Figure 22:
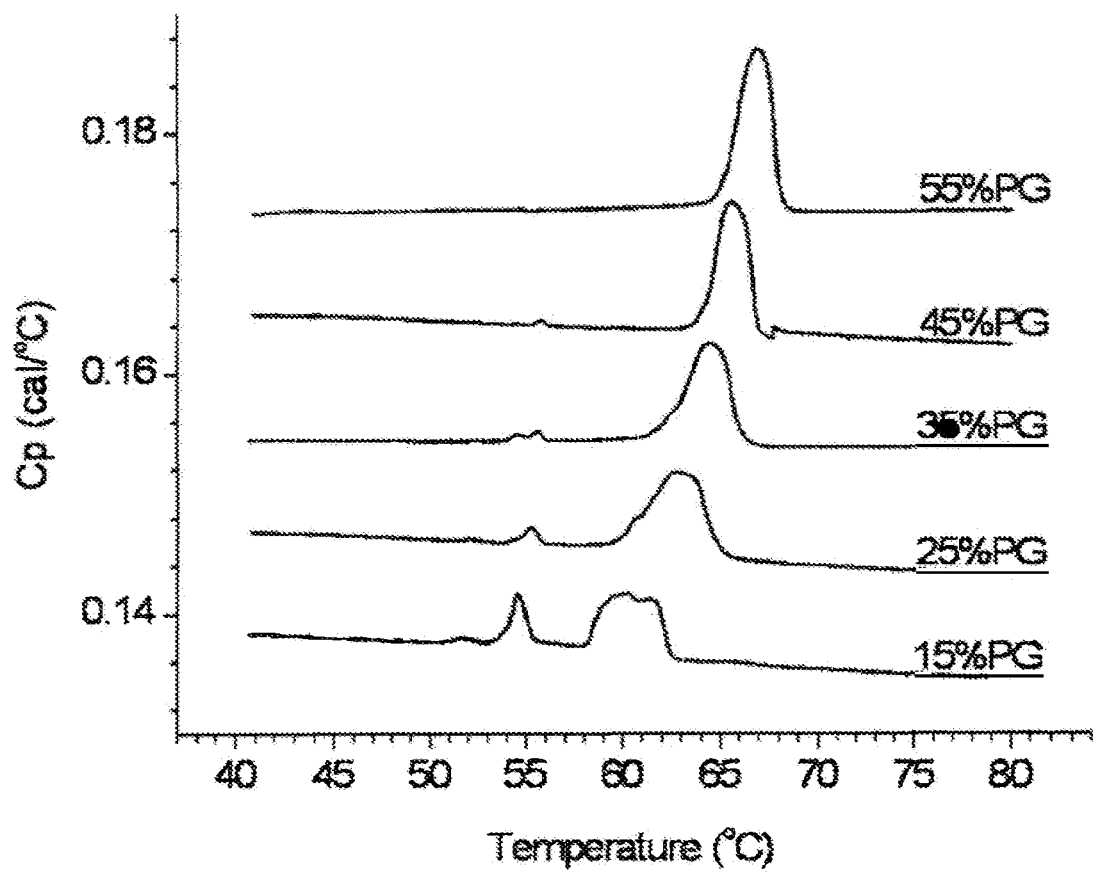

FIG. 22. DSC scan (1st scan) of Liposome encapsulated oxaliplatin formulations containing 5 mol % DSPE-PEG2000 and varying DSPC and DSPG concentration with 1 mM calcium gluconate on the exterior. Scan speed: 20° C./h.

Figure 23:
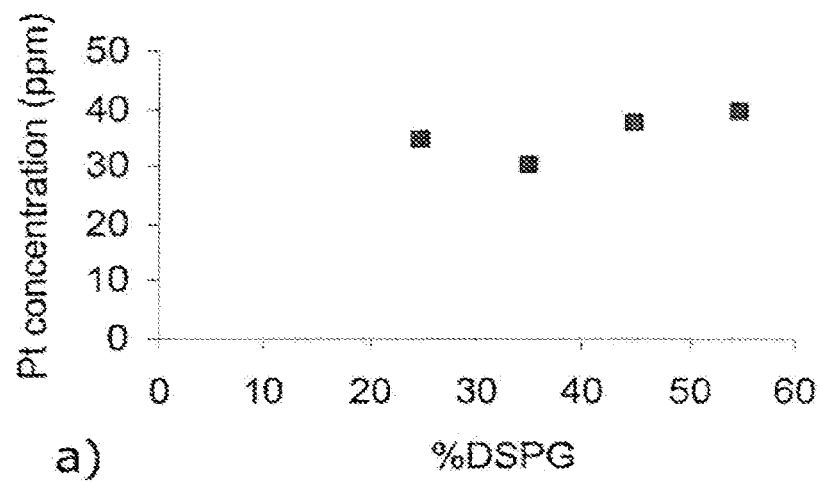
Figure 23:
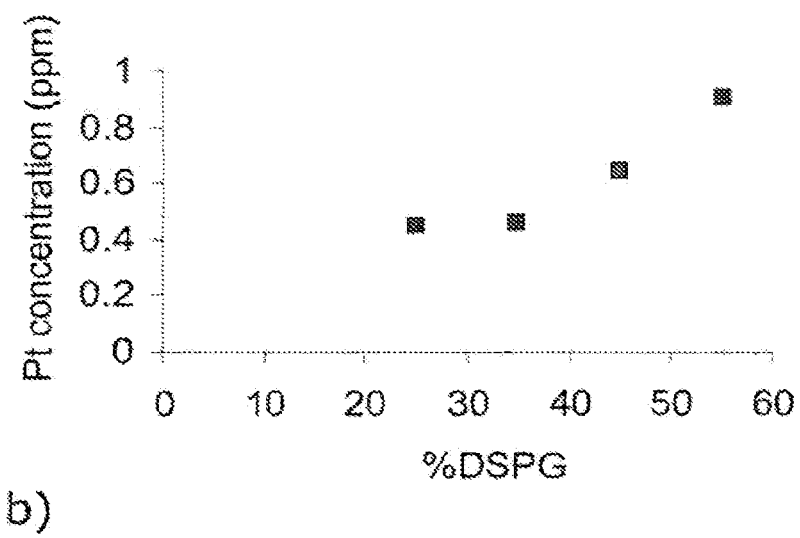

FIG. 23. Pt concentration in dialysate after a) 1st dialysis step and b) 2nd dialysis step (10% sucrose solution containing 1 mM calcium gluconate) of oxaliplatin encapsulated liposomes.

Figure 24:
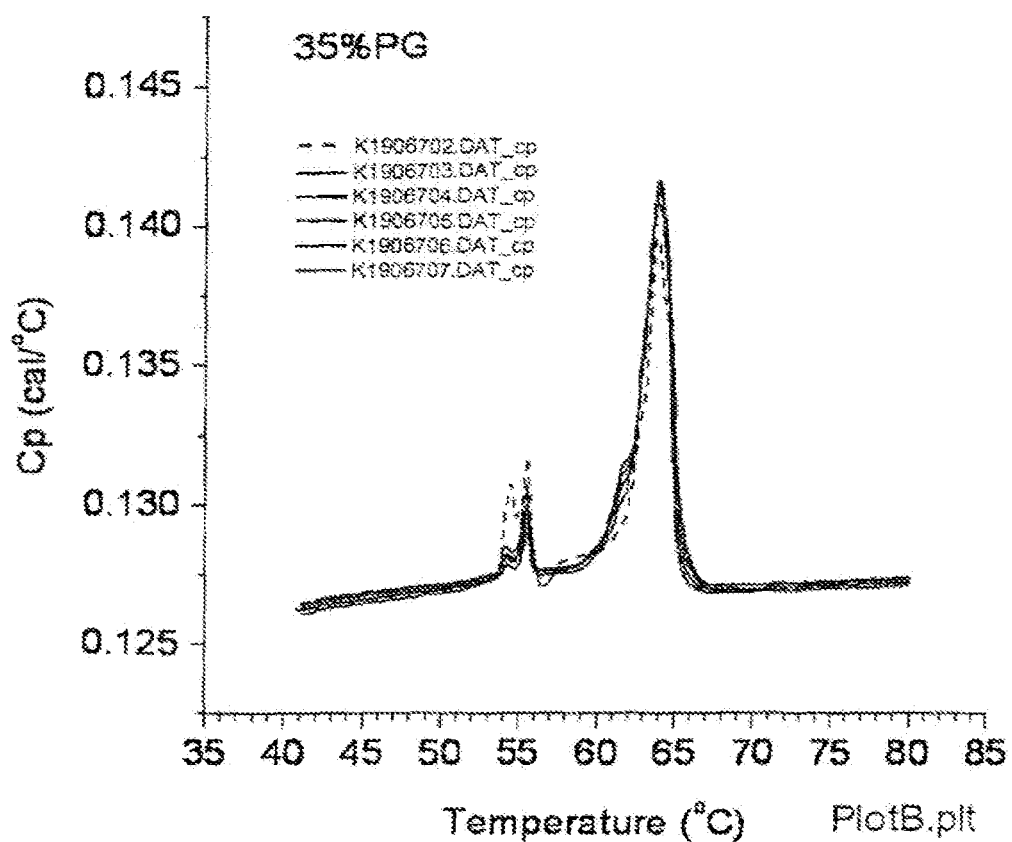

FIG. 24. 1.-6. DSC scans of Liposome encapsulated oxaliplatin (60/35/5 mol % DSPC/DSPG/DSPE-PEG2000) formulation with 1 mM calcium gluconate on both the interior and exterior. Scan speed: 20° C./h.

Figure 25:
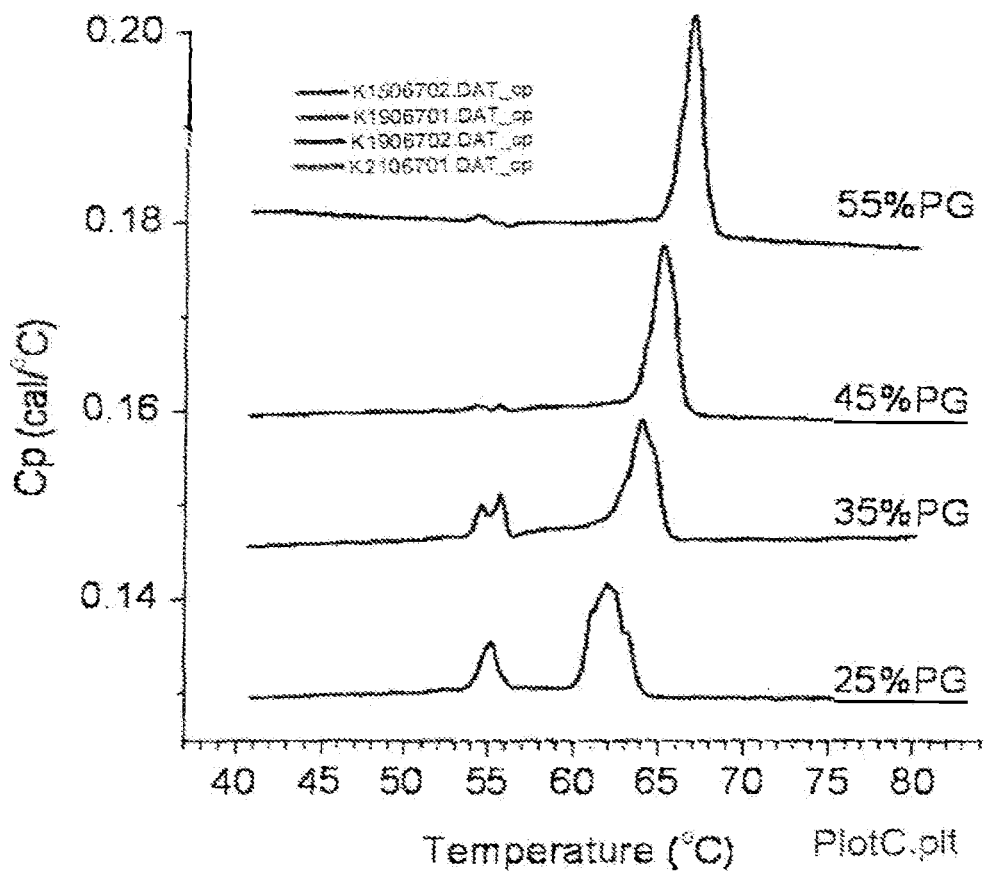

FIG. 25. DSC scan (1st scan) of Liposome encapsulated oxaliplatin formulations containing 5 mol % DSPE-PEG2000 and varying DSPC and DSPG concentrations with 1 mM calcium on both the interior and exterior. Scan speed: 20° C./h.

LIPOSOME OF THE INVENTION

One approach to obtaining triggered drug release in e.g. cancerous diseases is to utilize elevated levels of secretory phospholipase $A_2$ ($sPLA_2$) in the proximity of cancerous tissues. Thus, by carefully designing the lipid composition of the liposomes, they can be made degradable by $sPLA_2$ once accumulated in the tumour to give triggered release.

An object of the present invention is to provide liposomes and liposome formulations of improved stability which may deliver their payload (e.g. a drug) at the target site with reduced uncontrolled delivery and/or too early release due to leakiness of the liposome membrane. Another object is to provide liposomes and liposomal formulations with an increased stability during storage.

Anionic Lipids of the Liposome.

In a first aspect, the present invention provides a liposome comprising between 25% and 45% (mol/mol) of an anionic lipid. The present inventors have taken into account that the content of anionic lipid affects important characteristics of the liposome, such as the rate of $sPLA_2$ mediated lipid hydrolysis of the liposome and also the immune response toward the liposome.

As the content of anionic lipid increases, so does the rate of lipid hydrolysis by $sPLA_2$ (and the release of drug). It has been demonstrated that a reasonable rate of hydrolysis can be achieved by anionic lipid content between 25% and 45%. Thus, in one embodiment, the content of anionic lipid is at least 25%. In another embodiment, the content of anionic lipid is no more than 45%. In yet another embodiment, the anionic lipid content of the liposome is selected from the group consisting of between 25% and 45%, 25-42%, 28% and 42%, 30% and 40%, 32% and 38% and 34% and 36%. When referring to % content, reference is to mol/mol %, unless specifically mentioned otherwise.

As mentioned, also the immune response toward the liposomes is affected by the content of anionic lipid. Thus, the clearance rate of the liposome in body may be reduced by keeping the content of the anionic lipid in the liposome below a certain level and the present inventors have recognized that the content of anionic lipid in the liposome can be used to strike a balance between hydrolysis rate of $sPLA_2$ and clearance by the reticuloendothelial system.

Preferably the anionic lipid is a phospholipid and preferably, the phospholipid is selected from the group consisting of PI (phosphatidyl inositol), PS (phosphatidyl serine), DPG (bisphosphatidyl glycerol), PA (phosphatidic acid), PEOH (phosphatidyl alcohol), and PG (phosphatidyl glycerol). More preferably, the anionic phospholipid is PG.

Hydrophilic Polymers

In a preferred embodiment, the liposome further comprises a hydrophilic polymer selected from the group consisting of PEG [poly(ethylene glycol)], PAcM [poly(N-acryloylmorpholine)], PVP [poly(vinylpyrrolidone)], PLA [poly(lactide)], PG [poly(glycolide)], POZO [poly(2-methyl-2-oxazoline)], PVA [poly(vinyl alcohol)], HPMC (hydroxypropylmethylcellulose), PEO [poly(ethylene oxide)], chitosan [poly(D-glucosamine)], PAA [poly(amino-acid)], polyHEMA [Poly(2-hydroxyethylmethacrylate)] and co-polymers thereof.

Most preferably the polymer is PEG with a molecular weight between 100 Da and 10 kDa. Particular preferred are PEG sizes of 2-5 kDa (PEG2000 to PEG5000), and most preferred is PEG2000.

The inclusion of polymers on liposomes is well known to the skilled artisan and can be used to increase the half-life of the liposomes in the bloodstream, presumably by reducing clearance by the reticuloendothelial system.

Preferably, the polymer is conjugated to the head group of phospatidyl ethanolamine. Another option is ceramide (even though this lipid is not hydrolyzable by $PLA_2$).

The polymer-conjugated lipid is preferably present at an amount of at least 2%. More preferably, the amount is at least 5% and no more than 15%. Even more preferably, the amount of polymer-conjugated lipid is at least 3% and no more than 6%. Liposomes containing anionic phospholipids and 52.5% DSPE-PEG2000 have increased tendency to aggregate in the presence of calcium.

This can usually be observed by formation of high viscous gel. Liposomes containing anionic phospholipids and >7.5% causes the liposomes to sediment or phase separate. Thus, another preferred window is between 2.5% and 7.5%.

Neutrally Charged Lipid Components in the Liposome

Preferably, the liposome of the invention also comprises an uncharged phospholipid selected from the group consisting of zwitterionic phospholipids comprising PC (phosphatidyl choline) and PE (phosphatidylethanolamine). Most preferably, the zwitterionic phospholipid is PC.

In contrast to anionic phospholipid, zwitterionic phospholipid serves as a charge neutral $sPLA_2$-hydrolyzable lipid component in the liposome. By combining zwitterionic- and anionic phospholipid in the same liposome, it is possible to adjust to a desired surface charge density which complies with both sufficiently high $sPLA_2$ hydrolysis and a low clearance rate in the blood.

The amount of zwitterionic phospholipid in the liposome is preferably between 40% and 75% and more preferably between 50 and 70%.

Ether-Phospholipids

Some or all of the phospholipids may be ether-phospholipids.

Thus, they may harbour an ether-bond instead of an ester-bond at the sn-1 position of the glycerol backbone of the phospholipid. When $sPLA_2$ hydrolyze this particular type of phospholipids, mono-ether lyso-phospholipids are produced and these are toxic to e.g. cancer cells. I.e. ether phospholipids may be seen as pro-drugs of mono-ether lyso-phospholipids and liposomes of the invention can be used to deliver such pro-drugs to the $sPLA_2$-enhanced environment of cancer cells, where the pro-drugs are activated by $sPLA_2$ hydrolysis. Ether-phospholipids have been described in EP 1254143 and WO 2006/048017, the contents of which are hereby incorporated by reference.

Other Pro-Drugs

The moiety released from the lipid by $sPLA_2$ to create a lysolipid may also be a drug. Thus, a liposome may comprise pro-drugs of mono-ether lysolipids, pro-drugs released from the lipid by $sPLA_2$ and other therapeutic agents, as further outlined below.

Stabilizing Agent

The liposome may also be stabilized by the inclusion of cholesterol as membrane component in the liposome. However, high amounts of cholesterol in the liposome have a negative effect on hydrolysis by $PLA_2$ and therefore it is preferred that the liposome comprises no more than 20% or 10% cholesterol. Even more preferably, the liposome comprises less than 1% cholesterol, less than 0.1% or does not comprise any cholesterol at all.

The alkyl chain length of the lipids comprising the liposome may be adjusted for optimal $PLA_2$ hydrolysis rate and minimum leakage of entrapped compound out of the liposome. Preferably, the alkyl chains are C18 or C16 saturated chains.

The liposomes of the invention are preferably prepared by the method of the third aspect, wherein liposomes are stabilized by exposure to divalent cations.

As described above, the liposomes may comprise pro-drugs of mono-ether lyso-lipids and/or of the moiety released from the lipid by $sPLA_2$ to create the lysolipid.

In a preferred embodiment, the liposomes comprise a bioactive compound such as a therapeutic agent (drug), which is not a pro-drug of mono-ether lysophospholipid or mono-ether lysophospholipid. The liposome may also comprise prodrugs of mono-ether lysophospholipid and a therapeutic agent. Preferred bioactive compounds are small molecules, peptides, proteins and nucleic acids such as plasmids and oligonucleotides. A preferred class of proteins is antibodies, more preferably monoclonal antibodies. Preferred oligonucleotides are aptamers, antisense oligonucleotides, microRNAs and siRNAs. A class of compounds of particular interest is small molecule antitumour agents such as anthracyclin derivatives, cisplatin, oxaliplatin, carboplatin, doxorubicin, paclitaxel, 5-fluoruracil, exisulind, cis-retinoic acid, suldinac sulphide, methotrexate, bleomycin and vincristine. Another class of particular interest is antibiotics and antifungals and yet another class is anti-inflammatory agents such as steroids and non-stereoids. The liposome may comprise 1, 2, 3 or more different bioactive compounds. In a preferred embodiment, the liposome comprise only 1 bioactive component.

In another embodiment, the liposome comprises a diagnostic agent. By "diagnostic agent" is meant an agent that supports the localisation of the target tissue and/or the diagnosis of the disease and/or condition. Non-limiting examples could be contrast agents, microparticles, radioactive agents, target specific agents such as e.g. agents that bind specifically to markers associated with the disease and/or condition, etc. It is clear to a skilled person that in some embodiments the invention relates to a liposome formulation wherein the liposome comprises at least one drug as well as a diagnostic agent.

Physical-Chemical Characteristics of the Liposomes of the Invention

The liposome can be unilamellar or multilamellar. Most preferably, the liposome is unilamellar. The diameter of the liposome should be between 50 and 400 nm, preferably between 80 and 160 nm and most preferable between 90 and 120 nm.

Preferably, the Poly Dispersity Index (PDI) of the liposomal formulation of the second aspect of the invention should not exceed 0.2 and more preferable be 0.15 or less or even more preferably 0.10 or less. A PDI value in this range expresses a relatively narrow particle size-distribution in the formulation.

As will be clear from the above, it is preferred that at least one of the lipids comprising the liposome is a substrate for $sPLA_2$ when present in the liposome.

In one embodiment, the liposome comprises lipids which are hydrolysed by $sPLA_2$ at the sn-3 position instead of at the sn-2 position. Such unnatural lipids and liposomes comprising unnatural lipids have been disclosed in WO 2006/048017, the content of which is hereby incorporated by reference.

Preferably, the liposomes of the invention are present in the liposomal formulation of the second aspect. Thus, they have been stabilized by exposure to divalent cations as described in the second aspect. In one embodiment, the liposomes have only been exposed to divalent cations after formation. I.e. the interior of the liposomes does not contain divalent cations. In another embodiment, only the interior of the liposomes comprise divalent cations.

The presence of divalent cations associated with the liposomes of the invention is not directly verifiable. However, the present inventors have described parameters that are indicative of whether the liposomes have been stabilized by divalent cations.

A DSC-scan of liposomal oxaliplatin (70/25/5 mol % DSPC/DSPG/DSPE-PEG2000) in the absence of a divalent cation gives a single transition temperature observed as one peak. If the scan is repeated, the transition temperature is shifted towards higher temperatures, which might be due to the release of oxaliplatin to exterior of the liposomes when passing transition temperature (FIG. 19). Repeated DSC scans of liposomes that have been exposed to a divalent cation have a more constant transition temperature. Thus, in one embodiment, the liposomes of the invention are characteristic in that repeated DSC-scans of the liposome gives a transition temperature that differs by no more than 2° C. between the first and the second scan. In another embodiment, the liposomes of the invention are characteristic in that repeated DSC-scans of the liposomes gives a transition temperature that differs less between the first and second scan than will the transition temperature of control liposomes of the same composition.

A DSC-scan of liposomal oxaliplatin (70/25/5 mol % DSPC/DSPG/DSPE-PEG2000) stabilized by exposure to a divalent cation gives a phase-separated transition temperature (two peaks in the scan; see e.g. FIG. 22). Thus, in one embodiment of the liposomes of the invention, the liposomes are characteristic in that a DSC-scan of the liposomes gives a phase-separated transition temperature.

Moreover, the transition temperature of liposomes is shifted towards higher temperatures by exposure to divalent cations and one method of determining whether (test) liposomes have been exposed to a divalent cation such as calcium is by determining the transition temperature of control liposomes of the same composition as the test liposomes, wherein said control liposomes have not been exposed to a divalent cation. Thus, in one embodiment, the liposomes of the invention are characteristic in that they have a higher transition temperature than control liposomes of the same composition which have not been exposed to divalent cations.

In another embodiment, the liposomes of the invention are characteristic in that the mean liposome size does not decrease more than 10% and more preferably not more than 5%, when they are exposed to 1 mM calcium. If they have not been previously exposed to calcium, they will shrink when exposed to calcium. One way of testing of testing whether test liposomes have been exposed to calcium is by comparison to control liposomes of the same composition, where it is known that they have not been exposed to calcium. Thus, in one embodiment, the liposomes of the invention are characteristic in that they display a degree of shrinkage when exposed to 1 mM calcium that is smaller than the degree of shrinkage for control liposomes of the same composition, which have not been previously exposed to divalent cations.

Liposomal Formulation

A second aspect of the invention is a liposomal formulation comprising liposomes of the invention. Preferably, the formulation also comprise a divalent cation at a concentration of at least 0.1 mM. The present inventors have discovered that the presence of a divalent cation (or previous exposure to) stabilizes the liposomes of the formulation leading to reduced leakage of bioactive compound out of the liposomes. However, it is experienced that the concentration of divalent cation should not exceed 10 mM and more preferably not exceed 5 mM as such concentrations can lead to aggregation of the liposomes and undesirable high viscosities. More preferably, the concentration of divalent cation is not above 1 mM and most preferably the concentration of divalent cation is between 0.1 mM and 1 mM (FIG. 3). A preferred divalent cation is calcium.

In a preferred embodiment, the divalent cation is selected from the group consisting of magnesium ($Mg^{2+}$), iron ($Fe^{2+}$), calcium ($Ca^{2+}$), beryllium ($Be^{2+}$), magnesium ($Mg^{2+}$), strontium ($Sr^{2+}$), barium ($Ba^{2+}$), and radon ($Ra^{2+}$).

Various divalent cations have been tested (data not shown) and the best effects are seen with $Ca^{2+}$, wherefore $Ca^{2+}$ is preferred in the formulation.

Furthermore, it is experienced that also the counterion of $Ca^{2+}$ is important in some instances. Therefore, in one embodiment, the counterion is selected from the group consisting of bulky anions such as an organic salt, preferably selected from the group consisting of gluconate, propionate or lactate. More preferably the counterion is gluconate.

The divalent cation may be distributed at the interior of the liposome, at the exterior of the liposome or both at the interior and the exterior of the liposome. The divalent cation may therefore be present in the hydration solution and/or in the solution wherein the liposome formulation is purified, suspended and/or stored. In a preferred embodiment, the divalent cation is distributed at the exterior of the liposome, but not at the interior of the liposome. In this embodiment, the divalent cation may be added after liposome formation.

The concentration of calcium salt to be employed may depend on the individual liposome formulation and the drug. Salts such as e.g. $CaCl_2$ or NaCl are often required at certain concentrations to stabilize the liposomes. However, oxaliplatin is unstable in the presence of some salts, such as e.g. NaCl, and cisplatin is unstable in the presence of salts of phosphates or in pure water. Thus, the type of salt selected and their concentration will have a significant impact on the vesicle forming properties, and accordingly, depending on the drug to be encapsulated various salts must be selected and different salt concentrations used for the preparation of a liposome formulation.

Preferably, the Poly Dispersity Index (PDI) of the liposomal formulation should not exceed 0.2 and more preferable be 0.10 or less. A PDI value in this range expresses a relatively narrow particle size-distribution in the formulation.

Conservation of the Liposome Formulation

In a preferred embodiment, the liposomal formulation further comprises a cryo- and/or lyo-protecting agent.

During storage of liposomes the phospholipids may undergo hydrolysis. One simple way of preventing decomposition of the phospholipids in the liposome formulation is by freezing or freeze-drying.

Freezing may however induce leakage of the liposome formulation and result in release of the encapsulated drug. Addition of a cryo-protecting agent may be necessary in order to prevent or reduce leakage from the liposome preparation after freezing. Thus, in some embodiments the invention relates to a liposome formulation further comprising a cryo-protecting agent. Examples of agents that may be used as cryo-protecting agents may without limitation be disaccharides such as sucrose, maltose and/or trehalose. Such agents may be used at various concentrations depending on the preparation and the selected agent such as to obtain an isotonic solution.

The liposome can also be freeze-dried, stored and the reconstituted such that a substantial portion of its internal contents are retained. Liposome dehydration generally requires use of a lyo-protecting agent such as a disaccharide (sucrose, maltose or trehalose) at both the inside and outside interfaces of the liposome bilayer. This hydrophilic compound is generally believed to prevent the rearrangement of the lipids in the liposome formulation, so that the size and contents are maintained during the drying procedure and through subsequent reconstitution. Appropriate qualities for such drying protecting agents are that they possess stereo chemical features that preserve the intermolecular spacing of the liposome bilayer components.

Method of Preparing a Liposomal Formulation

A third aspect of the invention is a method of preparing a liposomal formulation comprising the steps a) Preparing a lipid mixture by dissolving selected lipids in an organic solvent b) Hydrating the product of step a) with an aqueous hydration solvent so as to form liposomes c) Removing the organic solvent of step a) either before addition of the aqueous hydration solvent or after the addition of the aqueous hydration solvent Preferably, the organic solvent is removed before addition of hydration solvent.

The method of further comprising of high sheer mixing to reduce the size of the liposomes.

The method may further comprise a step of extruding the liposomes produced in step c) through a filter to produce liposomes of a certain mean size.

The method may also comprise a step of sonicating the liposomal formulation to produce liposomes of a certain size.

Preferably, the liposome is a liposome as described in the first aspect of the invention.

Liposomes may be loaded with at least one therapeutic agent by solubilizing the drug in the organic solvent or hydration solvent used to prepare the liposomes.

Alternatively, ionisable therapeutic agent can be loaded into liposomes by first forming the liposomes, establishing an electrochemical potential, e.g. by way of a pH gradient, across the outermost liposome layer, and then adding the ionisable therapeutic agent to the aqueous medium external to the liposome.

In a preferred embodiment, the hydration solvent comprises a divalent cation at a concentration of at least 0.1 mM and more preferably at a concentration between 0.1 mM and 5 mM and most preferably between 0.1 mM and 1 mM. Preferably, the divalent cation is $Ca^{2+}$. In another embodiment, the hydration solvent does not comprise a divalent cation. In this embodiment, it is preferred that the exterior water phase is changed to another exterior water phase comprising a divalent cation as described below.

In another embodiment, the method further comprises a step of changing the exterior water phase of the formulation. Initially, the water phase will comprise the hydration solvent. The exterior water phase may be changed by centrifugation, ultrafiltration, dialysis or similar in order to prepare a liposomal formulation comprising liposomes in a solution of defined composition of the exterior water phase. Preferably, bioactive compounds (therapeutic agents) are only present inside or attached to the liposomes and not as free compounds in solution. Preferably, the drug encapsulation in the liposomes should be >70%, more preferably >95% and most preferably >99%. The degree of drug encapsulation is the ratio of drug encapsulated to the total amount of drug in the formulation.

In a preferred embodiment, the exterior water phase is changed to another exterior water phase comprising a divalent cation at a concentration of at least 0.1 mM and more preferably at a concentration between 0.1 mM and 5 mM and most preferably between 0.1 mM and 1 mM. Preferably, the divalent cation is $Ca^{2+}$.

The present inventors have discovered that liposomes initially leak entrapped compound when being exposed to calcium. Moreover, the liposomes condense to give smaller particle diameters. However, after initial leakage the liposomes exposed to $Ca^{2+}$ displays reduced leakage as seen e.g. in case of incubation in cell media (e.g. McCoy media; FIG. 3). Because of initial leakage, dialysis and/or centrifugation is typically done to separate liposomes from leaked material. Also filtration may be done.

In a preferred embodiment of the second aspect, the liposomal formulation is produced by the method of the third aspect.

Medicaments

A fifth aspect of the invention is the liposome of the first aspect or the liposomal formulation of the second aspect for use as a medicament.

A sixth aspect of the invention is the liposome of the first aspect or the liposomal formulation of the second aspect used for treatment of conditions, wherein $PLA_2$ activity is increased. Such conditions are e.g. cancer and inflammatory diseases.

EXAMPLES

Example 1: Preparation of Liposome Encapsulated Cisplatin and Liposome Encapsulated Oxaliplatin Liposome encapsulated cisplatin and Liposome encapsulated oxaliplatin are liposome-drug formulations wherein the drug cisplatin or oxaliplatin is encapsulated in the aqueous compartment of the liposome. The liposome drug formulations are composed of the drug encapsulated in a lipid mixture made of 5 mol % mPEG2000-disteoryl-phospahtidylethanolamine (DSPE-PEG2000); 25 mol % disterorylphosphatidylglycerol (DSPG); and 70 mol % disteorylphosphatidylcholine (DSPC). The specific procedure for each formulation is outlined below.

Liposome Encapsulated Cisplatin

Phospholipids were dissolved in 9:1 (v/v) chloroform/methanol. The solvent of the dissolved lipid mixtures were then evaporated in a 65° C. hot water bath until visual dryness, under a stream of nitrogen gas. The samples were further dried under vacuum overnight.

Hydration liquid (solution of sodium chloride and calcium gluconate both of varying concentrations) containing cisplatin were added to the dried lipid mixture at a temperature of 65° C.-70° C. for the preparation of multilamellar vesicles (MLV). The lipid suspensions were kept at 65-70° C. for at least 30 min. in order to ensure complete hydration. During this period, the lipid suspensions were vortex every 5 min. Large unilamellar vesicles (LUV) were prepared by 5 min. sonication at 65° C. of the MLV followed by extrusion through a 100 nm pore size polycarbonate filters at 65-70° C. LUV were subsequently transferred to dialysis cassettes (MWCO: 10 kDa) in order to remove untrapped cisplatin.

Liposome Encapsulated Oxaliplatin

Phospholipids were dissolved in 9:1 chloroform/methanol. The dissolved lipid mixtures were then evaporated in a 65° C. water bath until visual dryness, under a stream of nitrogen. The samples were further dried under vacuum overnight.

Hydration buffer (10% sucrose solution with varying concentrations of different calcium salts) containing oxaliplatin were added to the dried lipid mixture for the preparation of multilamellar vesicles (MLV). The lipid suspensions were kept at 65-70° C. for at least 30 min. in order to ensure complete hydration. During this period, the lipid suspensions were vortex every 5 min. large unilamellar vesicles (LUV) were subsequently prepared by 5 min. sonication at 65-70° C. of the MLV followed by extrusion through a 100 nm pore size polycarbonate filters ten times at 65-70° C. LUV were subsequently transferred to dialysis cassettes (MWCO: 10 kDA) in order to remove un-trapped oxaliplatin.

Estimates for the Pt content exterior to Liposome encapsulated cisplatin or Liposome encapsulated oxaliplatin is based on sample equilibration followed by a step of separation by centrifuge filtration. The Pt contents are quantified by use of ICP-MS.

TABLE 1

Cisplatin content in liposomal cisplatin formulation with varying content of Calcium gluconate.

| Calcium gluconate (mM) | Cisplatin content (mg/ml) |
|---|---|
| 0 | 1.10 |
| 0.10 | 0.49 |
| 1.00 | 0.77 |

TABLE 2

Oxaliplatin content in liposomal oxaliplatin formulation with varying content of Calcium gluconate.

| Calcium gluconate (mM) | Oxaliplatin content (mg/ml) |
|---|---|
| 0 | 0.40 |
| 0.01 | 0.45 |
| 0.10 | 0.82 |
| 1.00 | 1.24 |
| 5.00 | 1.01 |

Example 2: Stability of Oxaliplatin in Hydration Solution

Figure 1:
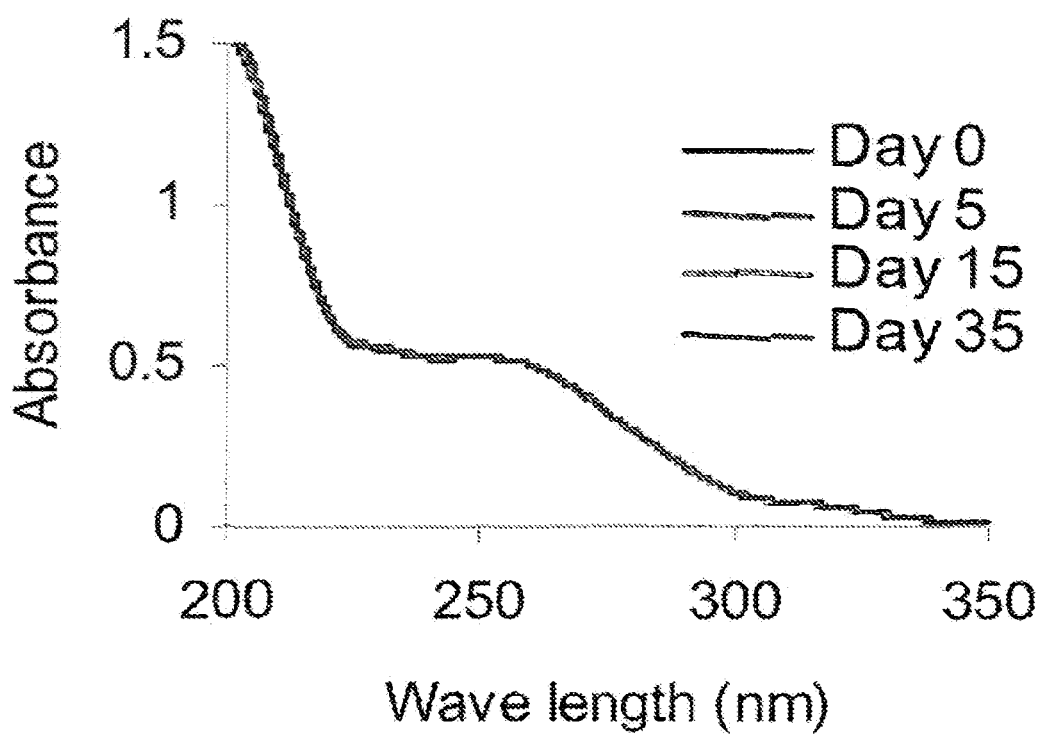
Figure 2:
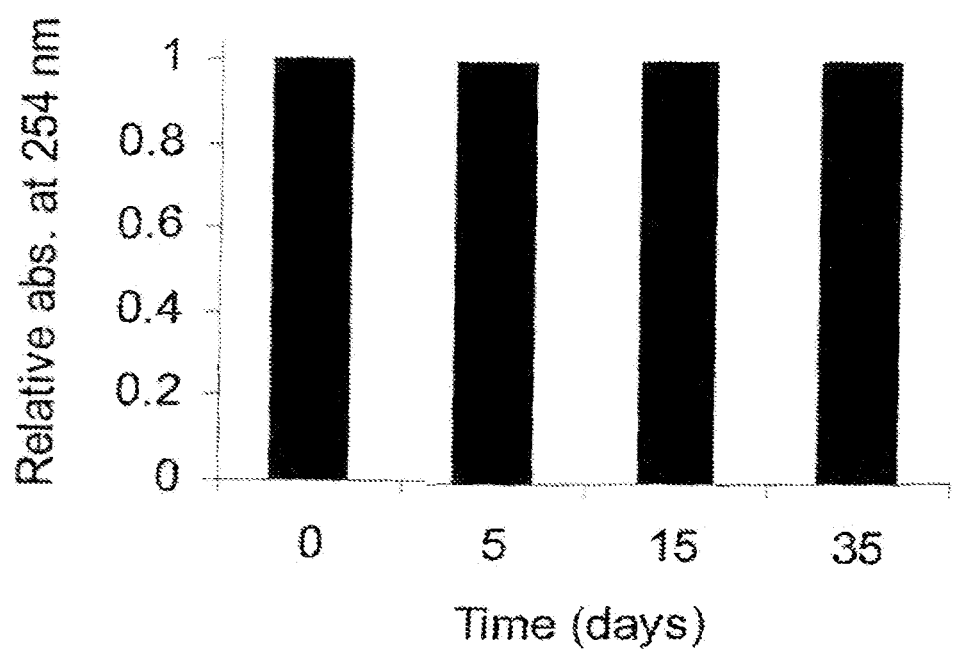

Oxaliplatin was dissolved in a hydration solution containing 10% sucrose and 1 mM Calcium gluconate (10 mg/ml). Sucrose was added to obtain an osmolarity approximately corresponding to physiological salt concentration. Stability of oxaliplatin in the hydration solution was followed by UV measurement. Samples were taken continually during storage at room temperature. Sample concentration measured was 0.1 mg/ml oxaliplatin. In order to follow the oxaliplatin stability a scan was performed from 200-350 nm (FIG. 1) and the absorbance at 254 nm was compared during storage (FIG. 2). Major changes in absorbance at 254 nm are usually related to oxaliplatin decomposition, which can easily be observed by dissolving oxaliplatin in solutions containing hydroxide and/or chloride ions. Several common buffer components such as phosphate, citrate, acetate, ethanolamine were also tested, however they were observed to decrease the absorbance at 254 nm (data not shown). Oxaliplatin dissolved in 10% sucrose solution containing 1 mM calcium gluconate showed to have practically no decomposition during storage at room temperature for at least 35 days.

Example 3: Stability of Liposome Encapsulated Oxaliplatin

Stability of Liposome encapsulated oxaliplatin formulations (70/25/5 mol % DSPC/DSPG/DSPE-PEG2000) was examined by measuring passive leakage of platinum species from the formulation stored in cell media (McCoy; FIG. 5A) at 37° C. Samples were taken at t=0 and t=24 hours. Leakage from liposomes was reported as the difference between the platinum content on exterior water phase immediately after addition to the cell media and after 24 hours incubation at 37° C.

Determination of Degree of Encapsulation:
1. 50 µl liposomal formulation is diluted in McCoy to a total volume of 5 ml.
2. Tube containing the diluted formulation is stored at 37° C. for 24 h.
3. 2 ml diluted sample (0 h and 24 h) is loaded onto Millipore centricon YM-30 filters, which are spun for 20 min at 15° C. and 2500 g.
4. 200 µl filtrate is collected and diluted to a total volume of 2 ml using McCoy.
5. 200 µl diluted sample is further diluted into a total volume of 2 ml.
6. The Pt content of samples is measured by ICP-MS. Standard curve is prepared in McCoy Media.

This cell media was used for the subsequent evaluation of the cytotoxic effect of Liposome encapsulated oxaliplatin on HT-29 colon carcinoma cells. Increased leakage from the liposomes upon storage in the cell media results in unspecific cytotoxicity. Formulation should have minimal cytotoxicity when it is has not undergone sPLA$_2$ hydrolysis. Varying concentrations of calcium gluconate (0-5 mM) in the Liposome encapsulated oxaliplatin formulation were examined for their ability to stabilize the liposomes (FIG. 5).

It was clearly demonstrated that formulations prepared with increasing concentration of calcium gluconate up to 5 mM increased stability of Liposome encapsulated oxaliplatin in McCoy media as the leakage from the liposomes decreased (FIG. 3). The initial degree of encapsulation (measured immediately after addition to the cell media) also increased with increasing concentrations of calcium gluconate. In order to examine if the stabilizing effect observed from calcium gluconate on the liposome formulation was related to calcium or gluconate, it was further examined whether other calcium or gluconate containing compounds were able to stabilize the Liposome encapsulated oxaliplatin formulation. As demonstrated in the table below it was evident that other calcium compounds were also capable of stabilizing the liposome formulation, whereas sodium gluconate was not. Calcium lactate and calcium propionate has similar stabilizing effect on the formulation as compared to calcium gluconate. These results suggest that calcium is responsible for the stabilizing effect on the liposome formulations.

TABLE 3

Test of different salts

| Liposome encapsulated oxaliplatin formulation (70/25/5 mol % DSPD/DSPG/DSPE-PEG2000) | Oxaliplatin (mg/ml) | DOE t = 0 h (%) | DOE t = 24 h (%) | Leakage (%) |
|---|---|---|---|---|
| 1 mM Sodium gluconate | 0.64 | 68 | 55 | 13 |
| 1 mM Calcium lactate | 0.80 | 99 | 98 | 1 |
| 1 mM Calcium propionate | 1.22 | 99 | 98 | 1 |

It was furthermore examined how the liposome formulation was affected by the presence of calcium gluconate on interior or exterior only. As demonstrated in the table below, it was quite evident that liposome formulation containing calcium on the interior only is not very good at stabilizing the liposome oxaliplatin formulation. Having calcium on the exterior only was demonstrated to stabilize the liposome formulation quite well.

TABLE 4

Test of localization of calcium gluconate

| Liposome encapsulated oxaliplatin formulation (70/25/5 mol % DSPD/DSPG/DSPE-PEG2000) | Oxaliplatin (mg/ml) | DOE t = 0 (%) | DOE t = 24 h (%) | Leakage (%) |
|---|---|---|---|---|
| 1 mM Calcium gluconate, interior | 0.61 | 68 | 46 | 22 |
| 1 mM Calcium gluconate, exterior | 0.64 | 96 | 92 | 4 |
| 1 mM Calcium gluconate, interior + exterior | 1.51 | 100 | 99 | 1 |

Example 4: Anticancer Ether Lipids

Ether phospholipids were used to prepare a liposome formulation of oxaliplatin encapsulated in a lipid mixture (25 mol % 1-O-octadecyl-2-octadecanoyl-sn-glycero-3-phosphoglycerol (1-O-DSPG), 70 mol % 1-O-octadecyl-2-octadecanoyl-sn-glycero-3-phosphocholine (1-O-DSPC) and 5 mol % dioctadecanoyl-sn-glycero-3-phosphoethanolamine-N-[methoxy-(polyethylene glycol)2000] (DSPE-PEG2000)) in a solution containing 10% sucrose and 1 mM calcium gluconate.

After storage in McCoy media at 37° C. for 24 hours only 4% leakage of oxaliplatin was observed.

Example 5: Cytotoxicity of Liposome Encapsulated Oxaliplatin

Cytotoxic activity of liposome encapsulated oxaliplatin was evaluated in colon carcinoma cells (HT-29) (FIG. 5). HT-29 cell line does not have the capability of secreting $PLA_2$. Free oxaliplatin was used as reference. HT-29 cells were treated for 6 h with oxaliplatin or Liposome encapsulated oxaliplatin in the presence or absence of $PLA_2$. $PLA_2$ from external source such as tear fluid was added to show that full release of oxaliplatin had occurred. With stable liposome formulation the HT-29 should not be affected by presence of such. In order to release the oxaliplatin from the liposome presence of a $PLA_2$ source is required. However with unstable liposome formulations leakage may occur, and thus affect HT-29 cells despite the absence of $PLA_2$. It is evident that when the concentration of calcium gluconate in the formulation is increased the leakage from the liposome decrease. The results are well correlated to the in vitro stability study (FIG. 3B) were it was observed that leakage from liposomes can be decreased by increasing the concentration of calcium gluconate.

Example 6 Stability of Liposomal Cisplatin Formulations Containing Calcium Gluconate Aim:
To examine the stability of liposomal cisplatin formulations (70/25/5 mol % DSPC/DSPG/DSPE-PEG2000) containing calcium gluconate in McCoy media. The goal is to find a formulation that has a minimum of leakage in McCoy media.

Protocol:
Liposome formulations (50 µl) were mixed with 4950 µl McCoy media and incubated at 37° C. for 24 h. Samples were taken at t=0 and t=24 h. Cisplatin formulation is prepared with varying concentrations of calcium gluconate.

Degree of Encapsulation:
1. 50 µl liposomal formulation is diluted in McCoy to a total volume of 5 ml.
2. Tube containing the diluted formulation is stored at 37° C. for 24 h.
3. 2 ml diluted sample (0 h and 24 h) is loaded onto Millipore centricon YM-30 filters, which are spun for 20 min at 15° C. and 2500 g.
4. 200 µl filtrate is collected and diluted to a total volume of 2 ml using McCoy.
5. 200 µl diluted sample is further diluted into a total volume of 2 ml.
6. The Pt content of samples is measured by ICP-MS. Standard curve is prepared in McCoy Media.

Results:

| Formulation | | Outside t = 0 (ppm) | DOE t = 0 h (%) | Outside ppm 24 | DOE t = 24 h (%) | Total (ppm) | Leakage (%) |
| --- | --- | --- | --- | --- | --- | --- | --- |
| Liposomal cisplatin | 100 uM Calcium gluconate | 9 | 98 | 30 | 92 | 390 | 5 |
| Liposomal cisplatin | 1 mM Calcium gluconate | 2 | 99 | 12 | 96 | 338 | 3 |

Liposome encapsulated cisplatin formulations containing 100 µM and 1 mM calcium gluconate had a reduced degree of leakage as compared to previous observations made with formulations prepared without the presence of calcium gluconate.

Figure 4:
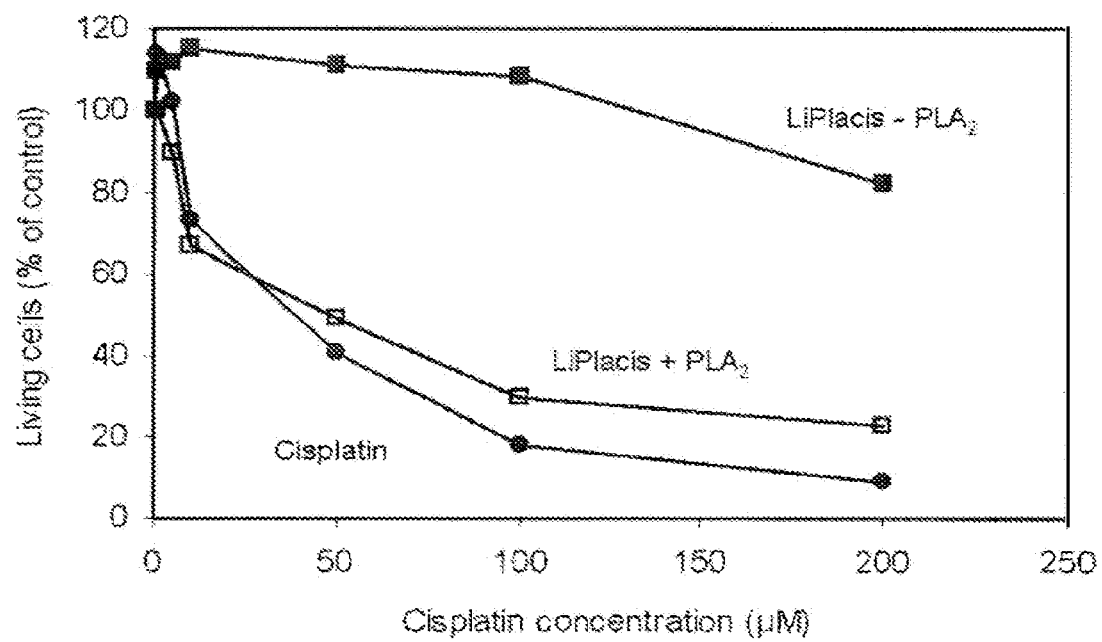
FIG. 4 illustrates the cytotoxicity of liposome (70/25/5 mol % DSPC/DSPG/DSPE-PEG2000) encapsulated cisplatin containing 1 mM calcium gluconate. HT-29 colon carcinoma cells were treated for 6 hours (37° C.) with cisplatin or Liposome encapsulated cisplatin in the presence or absence of s$PLA_2$.

This cell media was used for the subsequent evaluation of the cytotoxic effect of Liposome encapsulated cisplatin on HT-29 colon carcinoma cells (FIG. 4 and FIG. 6).

It is evident that when the concentration of calcium gluconate in the formulation is increased the leakage from the liposome decrease. The results are well correlated to the in vitro stability study (FIG. 3A) were it was observed that leakage from liposomes can be decreased by increasing the concentration of calcium gluconate.

Example 7, Effect of Calcium on Liposome Encapsulated Oxaliplatin formulation Aim: To examine the effect of adding or diluting Liposome encapsulated oxaliplatin formulation with a calcium gluconate solution.

Liposome encapsulated oxaliplatin formulation was prepared without calcium (10% sucrose on interior and exterior). Liposome encapsulated oxaliplatin formulation was diluted in varying concentrations of calcium (Lipid concentration maintained at 0.84 mM). Samples were equilibrated 24 h, and degree of encapsulation (DOE; %) and particle sizes were measured.

A suspension of liposomes (70/25/5 mol %, PC/PG/PE-PEG) containing 0.5 mol % of 1,2-dipalmitoyl-phosphatidylethanolamine with the fluorescent probe 7-nitrobenz-2-oxa-1,3-diazol-4-yl covalently linked to the head group (NBD-PE) (Fluka, Buchs, Switzerland) was prepared in 10% sucrose. The NBD probe molecules were excited at 465 nm and the peak of the emission wavelength was observed at 535 nm using a SLM DMX-1000 spectrofluorometer. A 2.5 mL aliquote of 0.1 mM freshly prepared lipid suspension was placed in a cuvette at constant temperature (25° C.), and equilibrated for 5 min prior to addition of irreversible dithionite quencher to the outer aqueous phase. Rapid sample mixing was attained in the cuvettes with magnetic stir bar. The time dependent decay of the fluorescence intensity was monitored after the addition of 30 µL freshly prepared sodium dithionite (1M $Na_2S_2O_4$ in 1M Trizma buffer stock solution). After 300 sec 30 µl 10 mM Calcium gluconate is added. Subsequent addition of 10 µl 10% Triton X-100 to the liposome preparations resulted in complete quenching of NBD-PE fluorescence within seconds.

Results

TABLE 1

Particle size analysis of liposomal oxaliplatin formulation (70/25/5 mol % DSPC/DSPG/DSPE-PEG2000) stored in various concentrations of calcium gluconate (24 h at room temperature). Lipid content maintained at 0.84 mM.

| $Ca^{2+}$ conc. [µM] | Sample 1 | Sample 2 | Sample 3 | Mean | SD |
|---|---|---|---|---|---|
| 0 | 115.9 | 111.4 | 111 | 112.7667 | 2.720907 |
| 1 | 114.3 | 113.1 | 113.1 | 113.5 | 0.69282 |
| 5 | 109.7 | 110.2 | 110.1 | 110 | 0.264575 |
| 10 | 108.5 | 107.5 | 107.5 | 107.8333 | 0.57735 |
| 50 | 103.8 | 101.5 | 101.9 | 102.4 | 1.228821 |
| 100 | 101.2 | 102.9 | 100.5 | 101.5333 | 1.234234 |
| 500 | 97.2 | 98.48 | 99.05 | 98.24333 | 0.947435 |
| 1000 | 101.8 | 103.5 | 101.9 | 102.4 | 0.953939 |
| 5000 | 109.4 | 107.4 | 106.5 | 107.7667 | 1.484363 |

TABLE 2

Pt analysis of Liposome encapsulated oxaliplatin (70/25/5 mol % DSPC/DSPG/DSPE-PEG2000) stored in various concentrations of calcium gluconate (24 h at room temperature). Lipid content maintained at 0.84 mM.

| $Ca^{2+}$ conc. [µM] | Outside [ppm] | Total [ppm] | Leakage (%) |
|---|---|---|---|
| 0 | 1.41 | 61.06 | 2.32 |
| 1 | 1.42 | 64.87 | 2.19 |
| 5 | 1.59 | 62.41 | 2.55 |
| 10 | 1.90 | 62.20 | 3.06 |
| 50 | 7.60 | 61.83 | 12.29 |
| 100 | 12.73 | 100.49 | 12.67 |
| 500 | 22.41 | 68.89 | 32.53 |
| 1000 | 21.67 | 67.89 | 31.91 |
| 5000 | 22.03 | 67.67 | 32.55 |

It could be observed that the particle size of liposomes decreased upon storage in solution containing varying concentrations of calcium (FIG. 7). Leakage from the formulation increased with an increase of calcium on the exterior (FIG. 8). Adding calcium to formulation containing NBD-PE probe, which had been quenched did not induce further quenching (FIG. 9). Results indicate that the addition of calcium does not induce transient permeability. These data indicate that calcium condensates the liposomal membrane, which causes particle size to decrease and release drug.

Example 8, Effect of $Ca^{2+}$ on Liposomal Oxaliplatin Formulation; Part I

Aim:

To examine the effect of only having calcium on the exterior water phase of various liposomal formulations containing DSPC, DSPG and DSPE-PEG2000 in terms of particle size, total Pt, DOE, and stability. To follow possible interaction between $Ca^{2+}$ and oxaliplatin with the membranes, DSC were conducted on the different formulations.

Protocol

Five different liposomal formulations of oxaliplatin were prepared without calcium on the interior. DSPG and DSPC contents were varied in the liposomal formulations as following:

1. 80:15:5 mol % PC/PG/PE-PEG
2. 70:25:5 mol % PC/PG/PE-PEG
3. 60:35:5 mol % PC/PG/PE-PEG
4. 50:45:5 mol % PC/PG/PE-PEG
5. 40:55:5 mol % PC/PG/PE-PEG 4 ml Liposome encapsulated oxaliplatin was sonicated (1 min/ml) at 75° C., followed by cooling in order to precipitate excess oxaliplatin. Supernatant was transferred to dialysis chambers (MWCO: 10 kDa), and dialyzed against 10% sucrose solution. 1.75 ml was filled in each chamber. The dialyzed sample was split into two portions and one was dialyzed further in beaker containing 10% sucrose solutions, and the other was dialyzed in beaker containing 10% sucrose solutions containing 1 mM calcium gluconate.

Particle sizes were followed after sonication, and after each step of dialysis.

The thermograms of the liposomal formulations (+/− Calcium gluconate) are compared.

The leakage during the $1^{st}$ and $2^{nd}$ dialysis step was monitored for liposomal formulations The stability of liposomal oxaliplatin formulations were tested in McCoy media (24 h, 37° C.).

Results

See FIGS. 10-22.

Particle Size Analysis (Size Given in Nm)

| % PG | After sonication | $1^{st}$ dialysis step (−calcium) | $2^{nd}$ dialysis step (−calcium) | $2^{nd}$ dialysis step (+calcium) |
|---|---|---|---|---|
| 15 | 100.2 ± 1.6 | 98.5 ± 1.5 | 102.8 ± 1.5 | 94.8 ± 1.4 |
| 25 | 97.4 ± 0.6 | 98.5 ± 0.5 | 112.6 ± 1.3 | 94.8 ± 0.5 |
| 35 | 105.7 ± 0.7 | 112.6 ± 1.7 | 122.5 ± 0.8 | 103.5 ± 1.1 |
| 45 | 80.8 ± 0.9 | 87.7 ± 0.5 | 98.3 ± 0.6 | 80.5 ± 0.8 |
| 55 | 82.5 ± 0.5 | 89.0 ± 0.6 | 104.4 ± 1.9 | 81.4 ± 1.3 |

Pt Analysis $1^{st}$ Dialysis Step (−Calcium)

| % PG | Outside (ppm) | DOE (%) | Total (ppm) | Ion count ratio ($Pt^{195}/P^{31}$) |
|---|---|---|---|---|
| 15 | 25.24 | 96.3 | 674.1 | 10.55 |
| 25 | 31.673 | 96.6 | 941.9 | 12.18 |
| 35 | 39.472 | 96.6 | 1178.1 | 14.54 |
| 45 | 54.115 | 94.2 | 927.4 | 11.07 |
| 55 | 43.60 | 95.1 | 898.0 | 10.93 |

$2^{nd}$ Dialysis Step (−Calcium)

| % PG | Outside (ppm) | DOE (%) | Total (ppm) | Ion count ratio ($Pt^{195}/P^{31}$) |
|---|---|---|---|---|
| 15 | 16.046 | 97.6 | 680 | 10.46 |
| 25 | 21.027 | 97.1 | 733 | 11.52 |
| 35 | 24.574 | 97.0 | 815 | 13.58 |
| 45 | 24.478 | 95.0 | 485 | 10.85 |
| 55 | 28.71 | 96.1 | 743 | 11.06 |

$2^{nd}$ Dialysis Step (+Calcium)

| % PG | Outside (ppm) | DOE (%) | Total (ppm) | Ion count ratio ($Pt^{195}/P^{31}$) |
|---|---|---|---|---|
| 15 | 9.919 | 98.0 | 495 | 8.49 |
| 25 | 14.137 | 97.3 | 517 | 7.18 |
| 35 | 11.258 | 98.1 | 599 | 7.91 |

-continued

| % PG | Outside (ppm) | DOE (%) | Total (ppm) | Ion count ratio ($Pt^{195}/P^{31}$) |
|---|---|---|---|---|
| 45 | 18.464 | 94.3 | 324 | 4.45 |
| 55 | 17.036 | 94.0 | 285 | 4.09 |

Stability in the McCoy Cell Media
Without Calcium in Dialysis Solution

| % PG | Outside t = 0 (ppm) | DOE t = 0 (%) | Outside t = 24 h (ppm) | DOE t = 24 h (%) | Total (ppm) |
|---|---|---|---|---|---|
| 15 | 95.5 | 84.70 | 149.3 | 76.08 | 624.2 |
| 25 | 214.7 | 27.37 | 166.3 | 43.74 | 295.7 |
| 35 | 184.1 | 55.77 | 271.6 | 34.74 | 416.2 |
| 45 | 168.3 | 58.73 | 242.0 | 40.65 | 407.7 |
| 55 | 320.5 | 47.51 | 356.2 | 41.65 | 610.5 |

With Calcium in Dialysis Solution

| % PG | Outside t = 0 (ppm) | DOE t = 0 (%) | Otside t = 24 h (ppm) | DOE t = 24 h (%) | Total (ppm) |
|---|---|---|---|---|---|
| 15 | 2.8 | 99.44 | 13.2 | 97.36 | 498.8 |
| 25 | 2.5 | 99.35 | 12.1 | 96.80 | 377.2 |
| 35 | 6.4 | 98.07 | 13.4 | 95.94 | 330.9 |
| 45 | 9.8 | 96.33 | 46.7 | 82.58 | 268.0 |
| 55 | 19.3 | 90.73 | 23.0 | 88.95 | 207.6 |

Discussion

Formulations were prepared without calcium on the interior, and with or without calcium on the exterior.

Particle sizes are observed to increase by raised PG content up to 45% PG in solutions only containing sucrose (FIG. 10). Contrary to this, by adding 1 mM calcium gluconate on the exterior the particle sizes are observed to decrease (FIG. 11). Formulation having the highest content of PG was observed to have largest variation in particle sizes in the absence of $Ca^{2+}$ (FIGS. 11+12).

There is practically no loss of oxaliplatin between $1^{st}$ and $2^{nd}$ dialysis if the dialysis solution is 10% sucrose in both dialysis steps (based on Ion count ratio ($Pt^{195}/P^{31}$)). Comparing the Pt/P levels of FIG. 14 for formulations containing calcium there is observed a decrease between $1^{st}$ and $2^{nd}$ dialysis step.

If calcium is present during dialysis there is observed a loss of oxaliplatin in comparison to formulation dialyzed in 10% sucrose solution. With increasing PG content in the formulation there is observed a decrease in oxaliplatin.

DOE (%) is usually higher for formulation with lower content of PG when dialyzed the same amount of time.

Plotting the particle size and total Pt concentration (FIG. 17) there seems to be a correlation. With increasing particle size there is observed a higher Pt content regardless lipid composition (varying DSPC and DSPG content).

Liposomes dialyzed in solution containing calcium gluconate are stable in McCoy media, whereas formulation dialyzed in 10% sucrose had major leakage of oxaliplatin when exposed to McCoy Media (FIG. 18).

DSC scan of a Liposome encapsulated oxaliplatin formulation of 35% PG showed that it was not possible to repeat the scan of the formulation when no calcium was present (FIG. 19). For each new scan the transition temperature continuously increased. When calcium was present on the exterior of the formulation, the transition temperature remained constant for each new scan (FIG. 21). Furthermore, with higher content of PG there was an increase in transition temperature (FIG. 20).

Transition temperature for Liposome encapsulated oxaliplatin formulation is in the range 60-70° C. It is therefore recommended that the extrusion temperature is maintained at 70° C.

Example 9, Effect of $Ca^{2+}$ on Liposomal Oxaliplatin Formulation; Part II

Aims:

To examine the effect of having calcium on both the interior and exterior of various liposomal formulations containing DSPC, DSPG and DSPE-PEG2000 in terms of particle size, total Pt, DOE, and stability. To follow possible interaction between $Ca^{2+}$ and oxaliplatin with the membranes, DSC were conducted on the different formulations.

Protocol:

Four different liposomal formulations of oxaliplatin were prepared with calcium gluconate on the interior. DSPC and DSPG contents were varied in liposomal formulation as following:

6. 70:25:5 mol % PC/PG/PE-PEG
7. 60:35:5 mol % PC/PG/PE-PEG
8. 50:45:5 mol % PC/PG/PE-PEG
9. 40:55:5 mol % PC/PG/PE-PEG 4 ml Liposome encapsulated oxaliplatin was sonicated (1 min/ml) at 75° C., followed by cooling in order to precipitate excess oxaliplatin. Supernatant is transferred to dialysis chambers (MWCO 3,500), and dialyzed against 10% sucrose solution containing 1 mM calcium gluconate. 3 ml was filled in each chamber. After 24 h the dialysis chamber is transfer to a new beaker containing 10% sucrose and 1 mM calcium gluconate.

Particle size is followed after sonication, and after each step of dialysis.

The thermograms of the liposomal formulations are compared.

The leakage during the $1^{st}$ and $2^{nd}$ dialysis step is monitored for liposomal formulations The stability of liposomal oxaliplatin formulations are tested in McCoy media (24 h, 37° C.).

Results
See FIGS. 23-25.
Particle Size Analysis (Size Given in Nm)

| % PG | After sonication | $1^{st}$ dialysis step (+calcium) | $2^{nd}$ dialysis step (+calcium) |
|---|---|---|---|
| 25 | 102.8 ± 1.18 | 95.5 ± 0.81 | 96.2 ± 0.91 |
| 35 | 143.1 ± 3.78 | 123.9 ± 1.52 | 127.7 ± 0.70 |
| 45 | 95.5 ± 0.48 | 87.5 ± 0.49 | 89.9 ± 0.75 |
| 55 | 93.9 ± 0.99 | 93.9 ± 0.50 | 99.9 ± 0.62 |

Pt Analysis
$1^{st}$ Dialysis

| % PG | Outside (ppm) | DOE (%) | Total (ppm) | Ion count ratio ($Pt^{195}/P^{31}$) |
|---|---|---|---|---|
| 25 | 3.5002 | 91.6 | 418.549 | 11.05 |
| 35 | 3.2822 | 96.8 | 1010.823 | 13.95 |

-continued

| % PG | Outside (ppm) | DOE (%) | Total (ppm) | Ion count ratio ($Pt^{195}/P^{31}$) |
|---|---|---|---|---|
| 45 | 4.8387 | 88.6 | 423.221 | 6.40 |
| 55 | 4.957 | 84.6 | 322.473 | 6.19 |

$2^{nd}$ Dialysis

| % PG | Outside (ppm) | DOE (%) | Total (ppm) | Ion count ratio ($Pt^{195}/P^{31}$) |
|---|---|---|---|---|
| 25 | 5.499 | 99.3 | 762.9 | 8.49 |
| 35 | 7.103 | 99.5 | 1346.8 | 13.84 |
| 45 | 8.057 | 98.5 | 526.62 | 6.36 |
| 55 | 16.29 | 97.2 | 579.596 | 5.98 |

Pt in Dialysate

| % PG | $1^{st}$ dialysis (ppm) | $2^{nd}$ dialysis (ppm) |
|---|---|---|
| 25 | 34.63 | 0.45 |
| 35 | 30.2 | 0.46 |
| 45 | 37.6 | 0.64 |
| 55 | 39.1 | 0.9 |

McCoy Stability

| % DSPG | Outside t = 0 (ppm) | DOE t = 0 (%) | Outside t = 24 h (ppm) | DOE t = 24 h (%) | Total (ppm) |
|---|---|---|---|---|---|
| 25 | 16.02 | 98.4 | 13.02 | 97.1 | 442.1 |
| 35 | 8.39 | 99.1 | 16.70 | 98.4 | 1024.2 |
| 45 | 9.23 | 97.8 | 16.56 | 95.6 | 377.6 |
| 55 | 16.02 | 94.9 | 23.25 | 92.7 | 316.4 |

General Conclusion:

Formulations were prepared with calcium on both the interior and exterior.

After the first dialysis step the particle sizes of the liposomes decrease for all formulations. From the first to the second dialysis step there is seen an increase in the particle size. Apparently, there is no correlation between the lipid composition and changes in particle sizes.

For all the formulations prepared there was observed higher Pt/P-ratio when calcium gluconate was included on the interior.

DSC scan of a Liposome encapsulated oxaliplatin formulation of 35% DSPG showed that the transition temperature remained constant for each new scan (FIG. 24). Furthermore, with higher content of PG there seems to be an increase in transition temperature (FIG. 25).

DOE (%) is usually higher for formulation with lower content of DSPG, when dialyzed the same amount of time.

The invention claimed is:

1. A composition comprising a therapeutic secretory phospholipase A2 (sPLA2) hydrolyzable liposome, wherein the liposome comprises:
   (a) 25% (mol/mol) of 1,2-distearoyl-sn-glycero-3-[phospho-rac-(1-glycerol)] (DSPG);
   (b) 70% (mol/mol) of 1,2-distearoyl-sn-glycero-3-phosphocholine (DSPC);
   (c) 5% (mol/mol) 1,2-distearoyl-sn-glycero-3-phosphoethanolamine-N-[methoxy(polyethylene glycol)-2000)] (DSPE-PEG);
   (d) less than 1% (mol/mol) cholesterol; and
   (e) oxaliplatin encapsulated in an interior aqueous phase of the liposome;

wherein the interior aqueous phase and an exterior aqueous phase of the liposome comprises 1 mM of $Ca^{2+}$ and wherein a counterion of $Ca^{2+}$ is selected from gluconate.

2. The liposome of claim 1, wherein the DSPE-PEG has a molecular weight between 100 Da and 10 kDa.

3. The liposome of claim 1, wherein the DSPG and/or the DSPC comprise saturated C18 alkyl chains.

4. The liposome of claim 1, wherein the liposome is a Large Unilamellar Vesicle (LUV) or has a diameter between 80 to 120 nm.

5. The liposome of claim 1, wherein at least one of the lipids in the liposome is a substrate for SPLA2.

6. The composition of claim 1 comprising more than one said liposome.

7. The composition of claim 6, wherein the polydispersity index of the composition is 0.20 or less.

8. A method for preparing the composition of claim 6 comprising:
   (a) preparing a lipid mixture by dissolving selected lipids in an organic solvent;
   (b) hydrating the product of step (a) with an aqueous hydration solvent so as to form liposomes;
   (c) removing the organic solvent of step (a) either before addition of the aqueous hydration solvent or after the addition of the aqueous hydration solvent; and
   d) introducing a hydration solvent comprising $Ca^{2+}$ gluconate at a concentration of 1 mM; and
   e) exchanging the hydration buffer on an exterior water phase of the formulation with an exterior water phase comprising $Ca^{2+}$ gluconate at a concentration of 1 mM.

9. The method of claim 8, wherein the organic solvent is removed before addition of the aqueous hydration solvent.

10. The method of claim 8, further comprising sonicating the composition to produce liposomes having an average size of between about 80 to 120 nm.

11. A method of treating a cancer in a subject in need thereof comprising administering the composition of claim 6 to the subject.

12. The method of claim 11, wherein the DSPG and/or the DSPC comprise saturated C18 alkyl chains.

13. The method of claim 11, wherein the liposome is an LUV or has a diameter between 80 to 120 nm.

* * * * *

UNITED STATES PATENT AND TRADEMARK OFFICE
CERTIFICATE OF CORRECTION

PATENT NO. : 11,173,178 B2
APPLICATION NO. : 16/786194
DATED : November 16, 2021
INVENTOR(S) : Anders Falk Vikbjerg et al.

Page 1 of 1

It is certified that error appears in the above-identified patent and that said Letters Patent is hereby corrected as shown below:

In the Claims

Column 20, Claim 1, Line 5, replace "distearoyl-sn-glycero" with --distearoyl-*sn*-glycero--;
Line 6, replace "pho-rac-(1-glycerol)]" with --pho-*rac*-(1-glycerol)]--;
Line 7, replace "distearoyl-sn-glycero" with --distearoyl-*sn*-glycero--;
Line 9, replace "distearoyl-sn-glycero" with --distearoyl-*sn*-glycero--;
Line 10, replace "(polyethylene     glycol)" with --(polyethylene glycol)--;
Line 17, replace "Ca2+ is selected from gluconate" with --Ca2+ is gluconate--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*